United States Patent
Yang et al.

(10) Patent No.: US 8,265,893 B2
(45) Date of Patent: *Sep. 11, 2012

(54) DIGITAL REORDERING UNIT, ULTRASONIC FRONT-END DEVICE AND OPERATING METHOD THEREOF

(75) Inventors: Bo Yang, Shenzhen (CN); Qinjun Hu, Shenzhen (CN); Xiaoyong Chen, Shenzhen (CN); Haitao Huang, Shenzhen (CN)

(73) Assignee: Shenzhen Mindray Bio-Medical Electronics Co., Ltd, Shenzhen (CN)

( * ) Notice: Subject to any disclaimer, the term of this patent is extended or adjusted under 35 U.S.C. 154(b) by 87 days.

This patent is subject to a terminal disclaimer.

(21) Appl. No.: 12/710,275

(22) Filed: Feb. 22, 2010

(65) Prior Publication Data

US 2010/0152581 A1 Jun. 17, 2010

Related U.S. Application Data

(63) Continuation of application No. 11/506,630, filed on Aug. 18, 2006, now Pat. No. 7,693,685.

(30) Foreign Application Priority Data

Feb. 28, 2006 (CN) .......................... 2006 1 0034089

(51) Int. Cl.
*G10K 11/00* (2006.01)
*G10K 15/00* (2006.01)
*H04B 11/00* (2006.01)
(52) U.S. Cl. ....................... 702/103; 702/189
(58) Field of Classification Search .................. 702/103, 702/189

See application file for complete search history.

(56) References Cited

U.S. PATENT DOCUMENTS

| 4,528,884 A | 7/1985 | Kawamoto et al. |
| 4,643,028 A | 2/1987 | Kondo et al. |
| 5,551,433 A | 9/1996 | Wright et al. |

(Continued)

FOREIGN PATENT DOCUMENTS

CN 1377630 A 11/2002

(Continued)

OTHER PUBLICATIONS

He Zhengquan et al. "A Design Method of the Switching Network for the Linear and Convex Array Transducer," Journal of UEST of China, vol. 24, No. 6; Dec. 1995, pp. 614-618.

(Continued)

*Primary Examiner* — Michael Nghiem
(74) *Attorney, Agent, or Firm* — Kory D. Christensen; Stoel Rives LLP

(57) ABSTRACT

A digital reordering unit, an ultrasonic front-end device and operating method thereof are provided. The ultrasonic front-end device may be connected between a probe and a detector of the ultrasonic system and controlled by a primary controller of the ultrasonic system, the ultrasonic front-end device having an ultrasonic transmission part and an ultrasonic reception part, wherein the ultrasonic transmission part includes a transmission beamformer and M transmission driving units, and has M transmission channels; the ultrasonic reception part includes M high-voltage isolation circuits, RC amplifiers, RC ADCs and a beamformer electrically serially connected and has RC reception channels, where RC=[N, 2N, 3N . . . p*N], N being an integer larger than or equal to 1, being characterized in that, M low-voltage analog switches and a network of resistors are serially connected between the M high-voltage isolation circuits and the RC amplifiers.

22 Claims, 13 Drawing Sheets

U.S. PATENT DOCUMENTS

| | | | |
|---|---|---|---|
| 5,617,862 A | 4/1997 | Cole et al. | |
| 5,882,307 A | 3/1999 | Wright et al. | |
| 5,982,309 A * | 11/1999 | Xi et al. | 341/101 |
| 6,029,116 A | 2/2000 | Wright et al. | |
| 6,174,286 B1 | 1/2001 | Ramamurthy et al. | |
| 6,705,997 B2 * | 3/2004 | Amemiya | 600/467 |
| 6,708,139 B2 * | 3/2004 | Rearick et al. | 702/185 |
| 7,693,685 B2 * | 4/2010 | Yang et al. | 702/183 |
| 2002/0075173 A1 * | 6/2002 | Nagata | 341/101 |
| 2005/0131297 A1 * | 6/2005 | Nishigaki et al. | 600/447 |
| 2005/0165307 A1 * | 7/2005 | Nishigaki et al. | 600/441 |
| 2006/0074317 A1 | 4/2006 | Satou et al. | |
| 2006/0074320 A1 * | 4/2006 | Yoo et al. | 600/472 |
| 2006/0085586 A1 * | 4/2006 | Birmiwal et al. | 710/306 |

FOREIGN PATENT DOCUMENTS

| | | |
|---|---|---|
| CN | 1646064 A | 7/2005 |
| CN | 1649545 A | 8/2005 |
| JP | 2001269336 A | 2/2001 |
| JP | 2001276064 A | 9/2001 |

OTHER PUBLICATIONS

Notice of Allowance of Feb. 5, 2010, for U.S. Appl. No. 11/506,630, filed Aug. 18, 2006.

* cited by examiner

DIGITAL REORDERING UNIT, ULTRASONIC FRONT-END DEVICE AND OPERATING METHOD THEREOF

RELATED APPLICATION

This application is a continuation of U.S. patent application Ser. No. 11/506,630, filed Aug. 18, 2006, now U.S. Pat. No. 7,693,685, which is hereby incorporated by reference herein in its entirety.

TECHNICAL FIELD

The invention relates to ultrasonic diagnostic techniques, especially to an ultrasonic front-end device and operating method thereof and a digital reordering unit for use in the ultrasonic front-end device, which is highly reliable, real-time and consumes less hardware resources.

BACKGROUND

The ultrasonic front-end device plays an important role in an ultrasonic diagnostic system. The number of reception channels in an ultrasonic diagnostic system determines the system cost as well as the system performance. There is a need to develop an ultrasonic front-end with good compatibility to satisfy the requirements of ultrasonic diagnostic systems with various performances, which may mitigate workload in development of an ultrasonic diagnostic system, thus decreasing cost in development of the ultrasonic diagnostic system and reducing future cost in maintenance of the ultrasonic diagnostic system.

When an ultrasonic diagnostic system is carrying out ultrasonic transmissions and receptions, due to the changes of the number of scan lines, the transmission and reception channels will choose to operate different array elements in the probe of the ultrasonic diagnostic system every time. Thus, the transmission and reception channels need to be reordered in both the transmission and reception processing. Reordering methods may be classified into analog reordering and digital reordering. Compared with analog reordering, digital reordering has the advantage of having higher reliability and lower cost. Therefore, it is of great importance for the ultrasonic front-end device to have a digital reordering unit, which is highly real time and consumes less hardware resources.

As shown in FIG. 1, a prior-art ultrasonic system 1 mainly comprises a probe 2, an ultrasonic front-end 3, a detector 4, a DSC (Digital Scan Conversion) unit 5, a display 6, and a primary controller 7, wherein the primary controller 7 is configured to perform man-machine interaction and control operations of the ultrasonic front-end device 3, the detector 4 and the DSC unit 5. The ultrasonic front-end device 3 includes two parts: an ultrasonic transmission part 31 and an ultrasonic reception part 32. The ultrasonic transmission part 31 comprises a transmission beamformer 311, a transmission drive unit 312 and a high-voltage analog switch 313. High-voltage transmission pulses originated from the ultrasonic transmission part 31 are fed into the probe 2, to activate the array elements 9 included in the probe 2 to emit ultrasonic waves. The probe 2 receives echoes of the ultrasonic waves, converts them into electric signals and provides the electric signals to the ultrasonic reception part 32. The ultrasonic receiving part 32 comprises a high-voltage analog switch 321, a high-voltage isolation circuit 322, an amplifier 323, an analog reordering unit 324, an ADC (Analog-to-Digital Converter) 325 and a reception beamformer 326. The electric signals received from the probe 2 are amplified, analog reordered and AD (Analog-to-Digital) converted and ultimately the received beam signals are formed. The detector 4 detects the beamformed signals received from the ultrasonic front-end 3, so as to acquire information to be displayed and feeds the information into the DSC unit 5. The DSC unit 5 coordinates transformation of the information and provides the transformed information to the display 6 for presentation. The analog reordering unit 324 is typically implemented with an expensive matrix of analog switches or a multi-stage analog switch.

The number of transmission and reception channels (especially the reception channels) in most conventional ultrasonic systems is less than the number of array elements Included in the probe, thus high-voltage analog switches have to be employed to select a suitable number of array elements from those included in the probe, for connection to their respective channels. The conventional ultrasonic systems may be classified into two types: type A and type B. For type A, the transmission and reception channels of an ultrasonic system share a single high-voltage analog switch and thus one high-voltage analog switch may be saved. However it brings difficulty in the implementation of synthetic aperture. For type B, the transmission and reception channels of an ultrasonic system use their own high-voltage analog switches, respectively, as shown in FIG. 1. Technical solutions disclosed in U.S. Pat. No. 5,817,862, No. 6,029,116, No. 5,882,307 and No. 5,551,433 relate to Type B ultrasonic systems, with an advantage of allowing the aperture of the reception channels and that of the transmission channels to have different sizes and thus provides a possibility to implement various aperture synthesis techniques.

The conventional ultrasonic system of FIG. 1 has several drawbacks. First, the use of high-voltage analog switches leads to high cost of the ultrasonic system. Second, the analog reordering unit adopts a multi-stage analog switch, thus affecting the quality of signal reception. Third, the use of high-voltage analog switches and multi-stage analog switches results in poor stability of the ultrasonic system.

There exists another type of ultrasonic system in the prior arts. This ultrasonic system is different from the one of FIG. 1 in that its ultrasonic transmission part has digital reordering function, but its ultrasonic reception part has no analog reordering unit and the reception beamformer has digital reordering function. As shown in FIG. 2, the ultrasonic transmission part 31 in the ultrasonic system 1 comprises a transmission beamformer 311, transmission driving units 312 and a high-voltage analog switch 313 connected in a sequential order. Referring to FIG. 3, the transmission beamformer 311 comprises a transmission parameter storing unit 3111 and a transmission parameter digital reordering unit 3112 whose output is provided to the transmission driving unit 312. As shown in FIG. 6, a digital reordering unit 40, such as the transmission parameter digital reordering unit 3112 of FIG. 3, comprises M M:1 multiplexers 41 followed by M corresponding D-type flip-flops (DFFs) 42, so as to implement a selection from M inputs to M outputs, where M denotes the number of array elements included in the probe of the ultrasonic system.

Furthermore, the ultrasonic reception part 32 comprises a high-voltage analog switch 321, a high-voltage Isolation circuit 322, amplifiers 323, ADCs 325 and a reception beamformer 326 with digital reordering function, all of them serially connected. The reception beamformers having digital reordering function in prior arts may be classified into two types. The first type of reception beamformer for performing digital reordering on the received parameters is shown in FIG. 4. The reception beamformer 326 comprises delay units 3281, a delay parameter read controller 3262, a delay parameter digital reordering unit 3283, apodization units 3284, an apodization parameter read controller 3265, an apodization parameter digital reordering unit 3288 and an adding unit 3267. The reception beamformer 328 delays, apodises and adds the signals received from the ADCs 325, to synthesize the received beam signals. The second type of reception beamformer for performing digital reordering on the received signals is shown in FIG. 5. The reception beamformer 328 comprises a signal digital reordering unit 3288, delay units 3261, a delay parameter read controller 3282, apodization units 3264, anapodization parameter read controller 3265 and an adding unit 3267. The reception beamformer 326 delays, apodises, reorders and adds the signals received from the ADCs 325, so as to synthesize the received beam signals. The prior art of the digital reordering method is shown in FIG. 6. M M:1 multiplexers are used to complete the selection from M Inputs to M outputs. This architecture is not optimal, because the delay from the inputs to outputs is large, and it consumes much hardware resource.

An ultrasonic diagnosing system disclosed in a U.S. patent application with publication No. 20060074317A has a function similar to digital reordering, but it fails to present a specific structure which may be real time and consumes less hardware resources.

A Chinese patent application with publication No. CN1649645A discloses an ultrasonic diagnostic equipment, which comprises an ultrasonic transmission part and an ultrasonic reception part. The ultrasonic reception part comprises a limiter (i.e. isolation circuit), low-voltage analog switches and ADCs. A cross point switch network is connected between these low-voltage switches and ADCs, for reordering and adding the received signals and providing the resultant signals to the ADCs for AD conversion. The ultrasonic diagnostic equipment has the drawbacks of incapable of implementing an ultrasonic system with a different number of channels.

SUMMARY OF THE INVENTION

The present invention is made in view of the drawbacks in the prior arts by providing an ultrasonic front-end device and its usage and a digital reordering unit for use in the ultrasonic front-end device. The ultrasonic front-end device is compatible with ultrasonic diagnostic systems having different numbers of reception channels and implemented on the same PCB (Print Circuit Board). According to the requirements of ultrasonic diagnostic systems with different numbers of reception channels, a corresponding number of amplifiers and ADCs may be soldered on the PCB to implement the corresponding number of reception channels.

In one aspect of the invention, a digital reordering unit for an ultrasonic front-end device is provided, comprising a plurality of 2:1 multiplexers and a plurality of DFFs coupled thereto correspondingly. A digital reordering unit with such a configuration implements a selection from M inputs to M outputs, to obtain a pipeline architecture from inputs to outputs, thus making the implementation of an ultrasonic system high-speed and real-time.

In another aspect of the invention, there is provided an ultrasonic front-end device for use in an ultrasonic system which is compatible with P types of reception channels, where P is an integer larger than or equal to 1; the ultrasonic front-end device being connected between a probe and a detector of the ultrasonic system and controlled by a primary controller of the ultrasonic system; the probe having M array elements, where M is an integer larger than or equal to 1, the ultrasonic front-end device having an ultrasonic transmission part and an ultrasonic reception part, wherein the ultrasonic transmission part comprises a transmission beamformer and M transmission driving units, and has M transmission channels; the ultrasonic reception part comprises M high-voltage isolation circuits, RC amplifiers, RC ADCs and a beamformer electrically connected in said order and has RC reception channels, where RC=[N, 2N, 3N, . . . p*N], N being an integer larger than or equal to 1; the ultrasonic front-end device being characterized in that, M low-voltage analog switches and a network of resistors are serially connected between the M high-voltage isolation circuits and the RC amplifiers, wherein M low-voltage analog switches are configured to electrically connect RC array elements of the M array elements in the probe and the RC respective reception channels in the ultrasonic reception part as the scan lines of the ultrasonic diagnostic system change, and the network of resistors configured to connect the RC reception channels connected by the M low-voltage analog switches with the RC amplifiersthe, the network of resistors comprising M Inputs IN[1, 2, 3, . . . , M] connected to the outputs of the low-voltage analog switches and RC outputs OUT[1, 2, . . . , RC] connected to the inputs of the RC amplifiers; the structure of the network of resistors can be expressed by the following formula: OUT[jj]=IN[jj+kk*RC], indicating that the output OUT[jj] and the input IN[jj+kk*RC] of the network of resistors are connected through resistors, where $1 \leq jj \leq RC$, $0 \leq kk \leq INT(M/RC)$, INT denotes taking the integer part, if jj+kk*RC>M, since such an input does not exist, there is no resistor connecting the Input and the output of the network of resistors; and a digital reordering unit included in the reception beamformer comprises a plurality of 2:1 multiplexers and a plurality of DFFs coupled thereto correspondingly.

In an embodiment, the low-voltage switches are single-stage analog switches.

In an embodiment, the connection between the network of resistors and the low-voltage analog switches and the amplifiers is implemented through resistors, wherein based on the number of RC, the corresponding resistors in the network of resistors are soldered with the low-voltage analog switches and the amplifiers.

In an embodiment, the transmission beamformer comprises a transmission parameter storage unit and a transmission parameter reordering unit, wherein the outputs from the transmission parameter reordering unit being provided to the transmission driving units, and the transmission parameter reordering unit comprising a plurality of 2:1 multiplexers followed with respective DFFs.

In an embodiment, the transmission beamformer sets and stores a set of ordered transmission parameters corresponding to the transmission channels respectively, to provide a binary control parameter B[K, K−1, K−2, . . . , 0] which varies as the scan lines of the ultrasonic system change, the control parameter controls an array of 2:1 multiplexers to convert the ordered transmission parameters into parameters for the current transmission channels, the array of 2:1 multiplexers comprises multiple stages, each of which stage having M 2:1 multiplexers, each bit of the parameter B controls M 2:1 multiplexers at a corresponding stage, where $2^{K+1} \geq M$, K being an integer larger than or equal to 0, wherein the inputs at the $0^{th}$ stage are the ordered transmission parameters for the M transmission channels; each bit of the parameter B is used to control M 2:1 multiplexers at a stage: if the bit is 0, the data from the "0" inputs of the 2:1 multiplexers are output, otherwise, the data on the "1" inputs of the 2:1 multiplexers are output the signals on the "1" inputs of the array of 2:1 multiplexers are shifted $2^K$ units rightward, the shift complies with the binary coding format and the outputs from the 2:1 multiplexers at the last stage are M digitally reordered transmission parameters.

In an embodiment, the reception beamformer that performs digital reordering on the reception parameters, the digital reordering unit included in the reception beamformer comprises delay parameter digital reordering units and apodization parameter digital reordering units, the delay parameter digital reordering units and apodization parameter digital reordering units each comprising a plurality of 2:1 multiplexers having a "0" Input and a "1" input and DFFs coupled thereto correspondingly.

In an embodiment, for the reception beamformer that performs digital reordering on the received signals, the digital reordering unit included in the reception beamformer comprises multiple stages of 2:1 multiplexers and DFFs connected thereafter, each stage comprising P*N 2:1 multiplexers having a "0" input and a "1" input and P*N DFFs coupled thereto correspondingly; based on a binary control parameter C[K, K−1, K−2, . . . , 0] which varies as the scan lines of the ultrasonic system change, an array of 2:1 multiplexers are controlled to perform digital reordering on the received signals, the array of 2:1 multiplexers including k+1 stages, each stage having P*N 2:1 multiplexers, where $2^{K+1} \geq P*N$, K being an integer larger than or equal to 0, wherein signals from the ADCs are received at the inputs of the P*N 2:1 multiplexers at the $0^{th}$ stage, each bit of the control parameter C is used to control M 2:1 multiplexers at a corresponding stage: if the bit is 0, the data from the "0" inputs of the 2:1 multiplexers are output, otherwise, the data from the "1" inputs of the 2:1 multiplexers are output; the signals on the "1" inputs of the array of 2:1 multiplexers are shifted $2^K$ units rightward, for example, the signals on the inputs of the multiplexers at the $0^{th}$ stage are shifted 1 unit rightward, the signals on the inputs of the multiplexers at the $1^{st}$ stage are shifted 2 units rightward, the signals on the inputs of the multiplexers at the $2^{nd}$ stage are shifted 4 units rightward, the signals on the inputs of the multiplexers at the $3^{rd}$ stage are shifted 8 units rightward, . . . , and the signals on the inputs of the multiplexers at the $K^{th}$ stage are shifted $2^K$ units rightward, the shift complies with the binary coding format and the outputs from the 2:1 multiplexers at the last stage are P*N digitally reordered signals.

In an embodiment, for the reception beamformer that performs digital reordering on the reception parameters, the digital reordering unit included in the reception beamformer comprises delay parameter digital reordering units and apodization parameter digital reordering units, the delay parameter digital reordering units and apodization parameter digital reordering units each comprising multiple stages of 2:1 multiplexers and DFFs connected thereafter, each stage having P*N 2:1 multiplexers having a "0" input and a "1" input and P*N DFFs coupled thereto correspondingly for the reception beamformer that performs digital reordering on the reception parameters, the reception beamformer sets and stores a set of ordered reception parameters corresponding to the reception channels respectively, to provide a binary control parameter C[K, K−1, K−2, . . . , 0] which varies as the scan lines of the ultrasonic system change, the control parameter controlling an array of 2:1 multiplexers to convert the ordered reception parameters into parameters for the current reception channels, the array of 2:1 multiplexers comprising K+1 stages, each stage having P*N 2:1 multiplexers, where $2^{K+1} \geq P*N$, K being an integer larger than or equal to 0, wherein the inputs of the P*N 2:1 multiplexers at the $0^{th}$ stage are set to the reception parameters for the corresponding reception channels each bit of the parameter C is used to control 2:1 multiplexers at a corresponding stage: if the bit is 0, the data from the "0" inputs of the 2:1 multiplexers are output, otherwise, the data on the "1" inputs of the 2:1 multiplexers are output; the signals on the "1" inputs of the whole array of 2:1 multiplexers are shifted $2^K$ units rightward, for example, signals on the inputs of the multiplexers at the $0^{th}$ stage are shifted 1 unit rightward, signals on the inputs of the multiplexers at the $1^{st}$ stage are shifted 2 units rightward, signals on the inputs of the multiplexers at the $2^{nd}$ stage are shifted 4 units rightward, . . . , and signals on the inputs of the multiplexers at the $K^{th}$ stage are shifted $2^K$ units rightward.

In this way, the ultrasonic diagnostic system using the ultrasonic front-end may achieves the following beneficial technical effects:

1. High-voltage analog switches are replaced by low-voltage analog switches, thus reducing cost of the ultrasonic system;
2. Ultrasonic systems with different numbers of channels may be accommodated through low-voltage analog switches and a network of resistors, thus improving the compatibility of the ultrasonic front-end of the ultrasonic diagnostic system; and
3. The digital sorting unit has a pipeline architecture from inputs to outputs, thus making the implementation of an ultrasonic system high-speed and real-time.

In still another aspect of the invention, there is provided a operating method of an ultrasonic front-end device in an ultrasonic diagnostic system, wherein the ultrasonic front-end device is compatible with P types of reception channels, where P is an integer larger than or equal to 1; the ultrasonic front-end device is connected between a probe and a detector of the ultrasonic system and controlled by a primary controller of the ultrasonic system, the probe comprising M array elements, where M is an integer larger than or equal to 1, the ultrasonic front-end device comprising an ultrasonic transmission part and an ultrasonic reception part, wherein the ultrasonic transmission part comprises a transmission beamformer and M transmission driving units, and has M transmission channels, and the ultrasonic reception part has RC reception channels, where RC=g[N, 2N, 3N . . . p*N], N being an Integer larger than or equal to 1, and comprises M high-voltage isolation circuits, RC amplifiers, RC ADCs and a beamformer electrically connected in said order, The method being characterized in that, M low-voltage analog switches and a network of resistors are serially connected between the M high-voltage isolation circuits and the RC amplifiers, the M low-voltage analog switches are configured to electrically connect RC array elements of the M array elements in the probe and the RC corresponding reception channels in the ultrasonic reception part as the scan lines of the ultrasonic system change; the network of resistors is configured to connect the RC reception channels connected by the M low-voltage analog switches with the RC amplifiers, the network of resistors comprises M inputs IN[1, 2, 3, . . . , M] connected to the outputs of the low-voltage analog switches and RC outputs OUT[1, 2, . . . , RC] connected to the inputs of the amplifiers, the structure of the network of resistors is expressed by the following formula: OUT[jj]=IN[jj+kk*RC], indicating that the output OUT[jj] and the input IN[jj+kk*RC] of the network of resistors are connected through resistors, where $1 \leq jj \leq RC$, $0 \leq kk \leq INT(M/RC)$, INT denotes taking the integer part, if j+kk*RC>M, since such an input does not exist, there Is no resistor connecting the input and the output of the network of resistors; and a digital reordering unit Included in the reception beamformer comprises a plurality of 2:1 multiplexers and a plurality of DFFs coupled thereto correspondingly, the method comprising the steps of:

(1) emitting pulses by the ultrasonic transmission part with transmission parameters, to activate the currently selected transmission array elements in the probe of the ultrasonic system to transmit ultrasonic waves;

(2) receiving echoes of the ultrasonic waves and converting them into electric signals by the currently selected reception array elements in the probe;

(3) receiving the electric signals from the probe by the high-voltage isolation circuits in the ultrasonic reception part;

(4) electrically connecting, by the M low-voltage analog switches in the ultrasonic reception part, RC array elements of the M array elements in the probe and RC corresponding reception channels in the ultrasonic reception part as the scan lines of the ultrasonic diagnostic system change;

(5) connecting, by the network of resistors, the RC reception channels connected by the M low-voltage analog switches with the RC amplifiers;

(6) amplifying and AD converting the received electric signals by the amplifiers and the ADCs in the ultrasonic reception part; and (7) digital reordering the reception parameters or the received signals, and beam forming by the beamformer in the ultrasonic reception part.

In an embodiment, the step (1) further comprises the sub-steps of: (1a) setting and storing, by the transmission beamformer in the ultrasonic transmission part, a set of ordered transmission parameters corresponding to the transmission channels; and (1b) providing, by the transmission beamformer, a binary control parameter B[K, K−1, K−2, . . . , 0] which varies as the scan lines of the ultrasonic system change; the parameter controls an array of 2:1 multiplexers to convert the ordered transmission parameters into parameters for the current transmission channels; the array of 2:1 multiplexers comprises a plurality of stages each having M 2:1 multiplexers, each bit of the parameter controls M 2:1 multiplexers at a corresponding stage, where $2^{K+1} \geq M$, K being an integer larger than or equal to 0; the inputs at the $0^{th}$ stage are the ordered transmission parameters for the M transmission channels; each bit of the parameter B is used to control M 2:1 multiplexers at a corresponding stage: if the bit is 0, the data on the "0" inputs of the 2:1 multiplexers are output, otherwise, the data on the "1" inputs of the 2:1 multiplexers are output; the signals on the "1" inputs of the array of 2:1 multiplexers are shifted $2^K$ units rightward, for example, the signals on the inputs of the multiplexers at the $0^{th}$ stage are shifted 1 unit rightward, the signals on the inputs of the multiplexers at the $1^{st}$ stage are shifted 2 units rightward, the signals on the inputs of the multiplexers at the $2^{nd}$ stage are shifted 4 units rightward, the signals on the inputs of the multiplexers at the $3^{rd}$ stage are shifted 8 units rightward, . . . , and the signals on the inputs of the multiplexers at the $K^{th}$ stage are shifted $2^K$ units rightward, the shift complies with the binary coding format, and the outputs from the 2:1 multiplexers at the last stage are M digitally reordered transmission parameters.

There are two types of digital reordering at the step (7): first, conduct digital reordering on the received signals while no digital reordering on the reception parameters; second, conduct digital reordering on the reception parameters while no digital reordering on the received signals.

In an embodiment, for the reception parameters, the digital reordering and beam forming at the step (7) comprises the substeps of: (7a) setting and storing a set of ordered reception parameters corresponding to the reception channels, by the reception beamformer in the ultrasonic reception part; and (7b) providing, by the reception beamformer, a binary control parameter C[K, K−1, K−2, . . . , 0] which varies as the scan lines of the ultrasonic system change, the control parameter controlling an array of 2:1 multiplexers to convert the ordered reception parameters into parameters for the current reception channels; the array of 2:1 multiplexers comprises multiple stages each having P*N 2:1 multiplexers, each bit of the parameter controls P*N 2:1 multiplexers at a corresponding stage, where $2^{K+1} \geq P*N$, K being an integer larger than or equal to 0, wherein all the inputs of the P*N 2:1 multiplexers at the $0^{th}$ stage are the reception parameters for the corresponding reception channels; each bit of the parameter C is used to control 2:1 multiplexers at a corresponding stage: if the bit is 0, the data from the "0" inputs of the 2:1 multiplexers are output, otherwise, the data from the "1" inputs of the 2:1 multiplexers are output; the signals on the "1" inputs of the whole array of 2:1 multiplexers are shifted $2^K$ units rightward, for example, the signals on the "1" inputs of the multiplexers at the $0^{th}$ stage are shifted 1 unit rightward, the signals on the "1" inputs of the multiplexers at the $1^{st}$ stage are shifted 2 units rightward, the signals on the "1" inputs of the multiplexers at the $2^{nd}$ stage are shifted 4 units rightward, . . . , and the signals on the "1" inputs of the multiplexers at the $K^{th}$ stage are shifted $2^K$ units rightward.

In an embodiment, for the received signals, the digital reordering and beam forming at the step (7) comprises a substep of: providing, by the reception beamformer, a binary control parameter C[K, K−1, K−2, . . . , 0] which varies as the scan lines of the ultrasonic system change, the control parameter controls an array of 2:1 multiplexers; the array of 2:1 multiplexers includes k+1 stages each having P*N 2:1 multiplexers, where $2^{K+1} \geq P*N$, K being an integer larger than or equal to 0, wherein signals from the ADCs are received by the inputs of the P*N 2:1 multiplexers at the $O^{th}$ stage, each bit of the control parameter C is used to control P*N 2:1 multiplexers at a corresponding stage: if the bit is 0, the data from the "0" inputs of the 2:1 multiplexers are output, otherwise, the data from the "1" inputs of the 2:1 multiplexers are output; the signals on the "1" inputs of the array of 2:1 multiplexers are shifted $2^K$ units rightward, for example, the signals on the inputs of the multiplexers at the $0^{th}$ stage are shifted 1 unit rightward, the signals on the inputs of the multiplexers at the $1^{st}$ stage are shifted 2 units rightward, the signals on the inputs of the multiplexers at the $2^{nd}$ stage are shifted 4 units rightward, the signals on the inputs of the multiplexers at the $3^{rd}$ stage are shifted 8 units rightward, . . . , and the signals on the inputs of the multiplexers at the $K^{th}$ stage are shifted $2^K$ units rightward, the shift complies with the binary coding format, and the outputs from the 2:1 multiplexers at the last stage are P*N digitally reordered signals.

The aforementioned technical solutions lead to implementation of a high-speed and real-time ultrasonic system, improvement in the compatibility for the ultrasonic front-end of the ultrasonic system and cost saving for the ultrasonic system.

DETAILED DESCRIPTION

Detailed descriptions will be made below to the invention with reference to embodiments shown in accompanying drawings.

Figure 1:
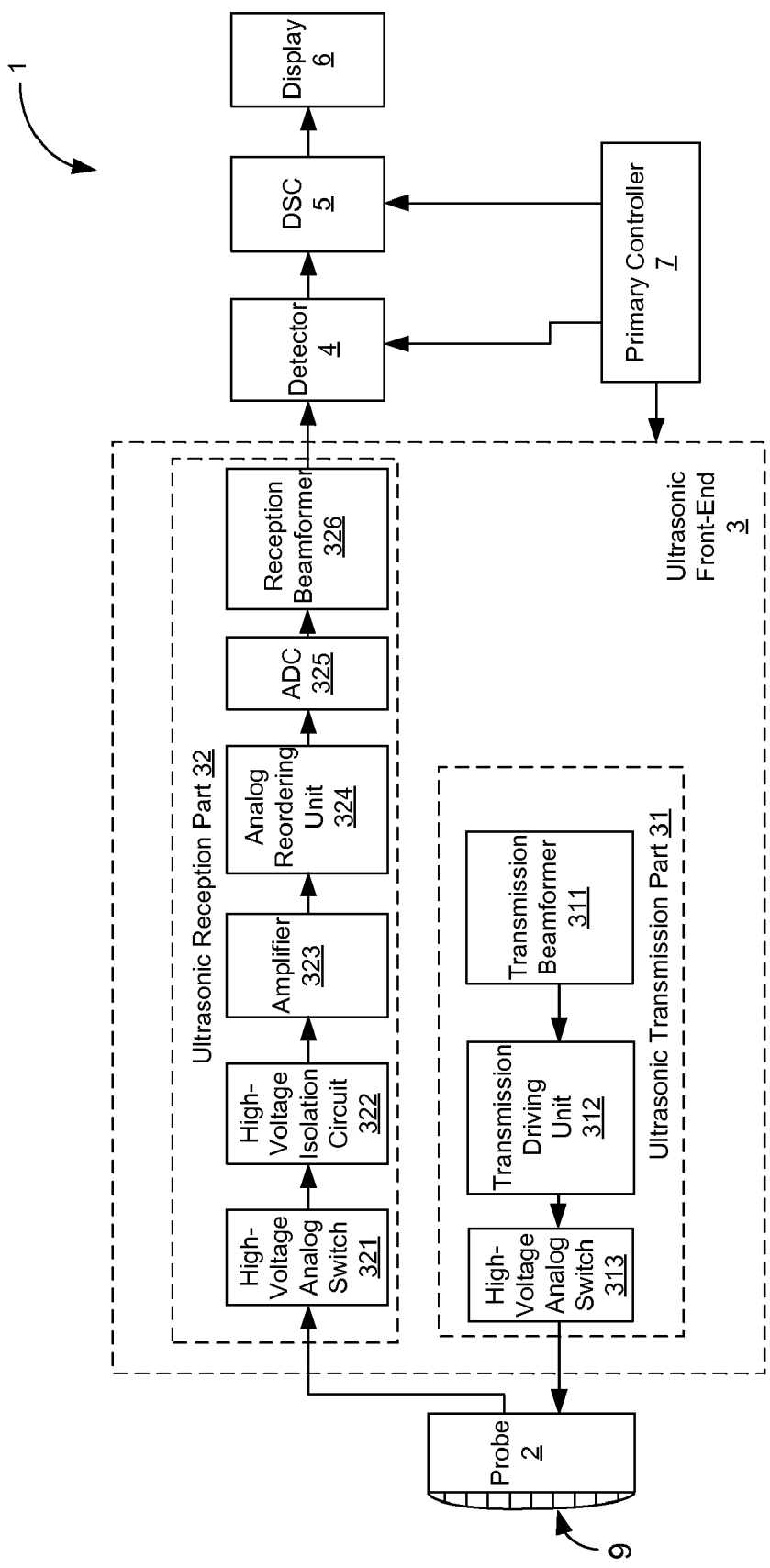
FIG. 1 is a block diagram showing the configuration of an ultrasonic system in prior arts.
Figure 2:
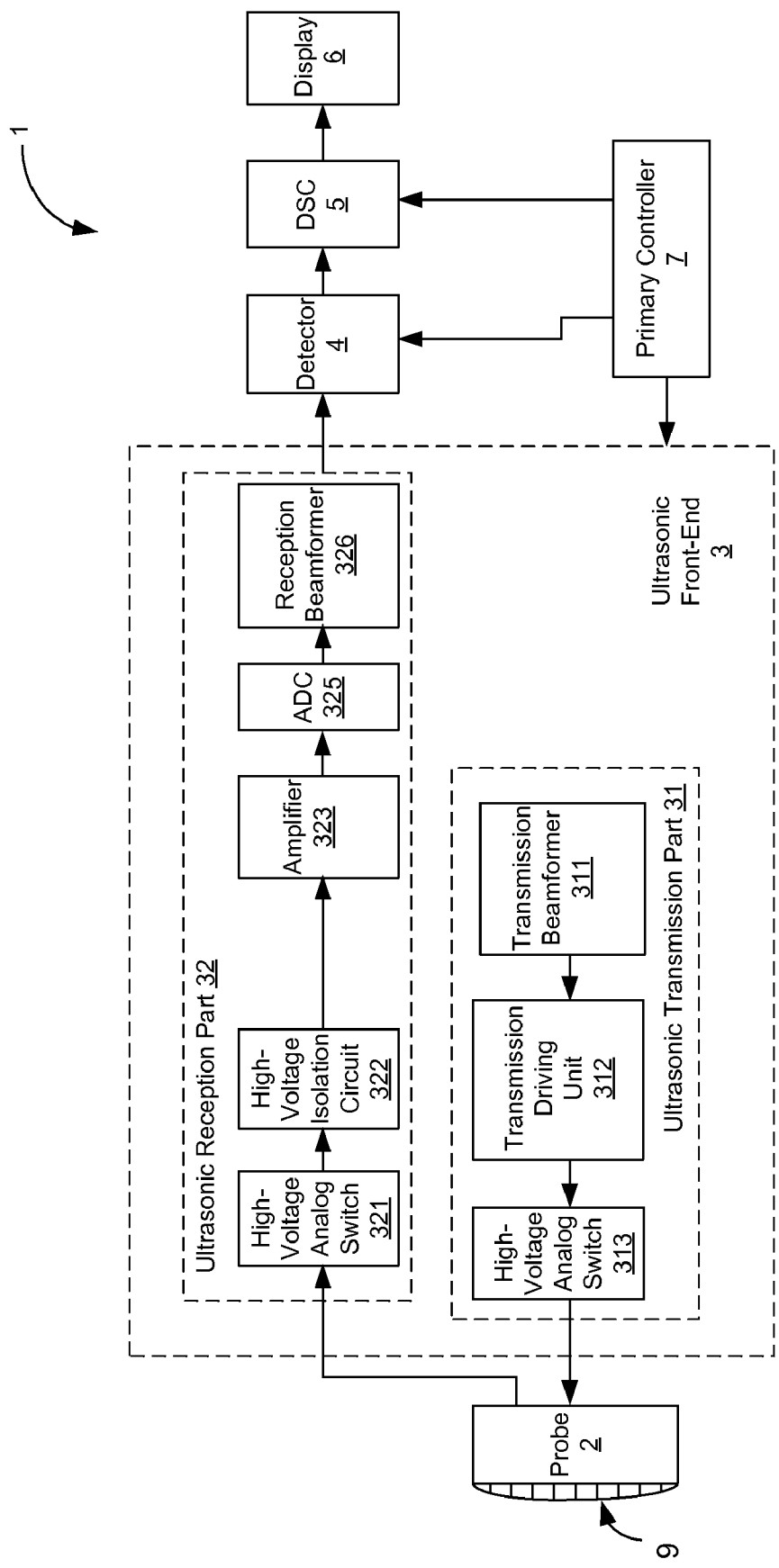
FIG. 2 is a block diagram showing the configuration of another ultrasonic system in prior arts.
Figure 3:
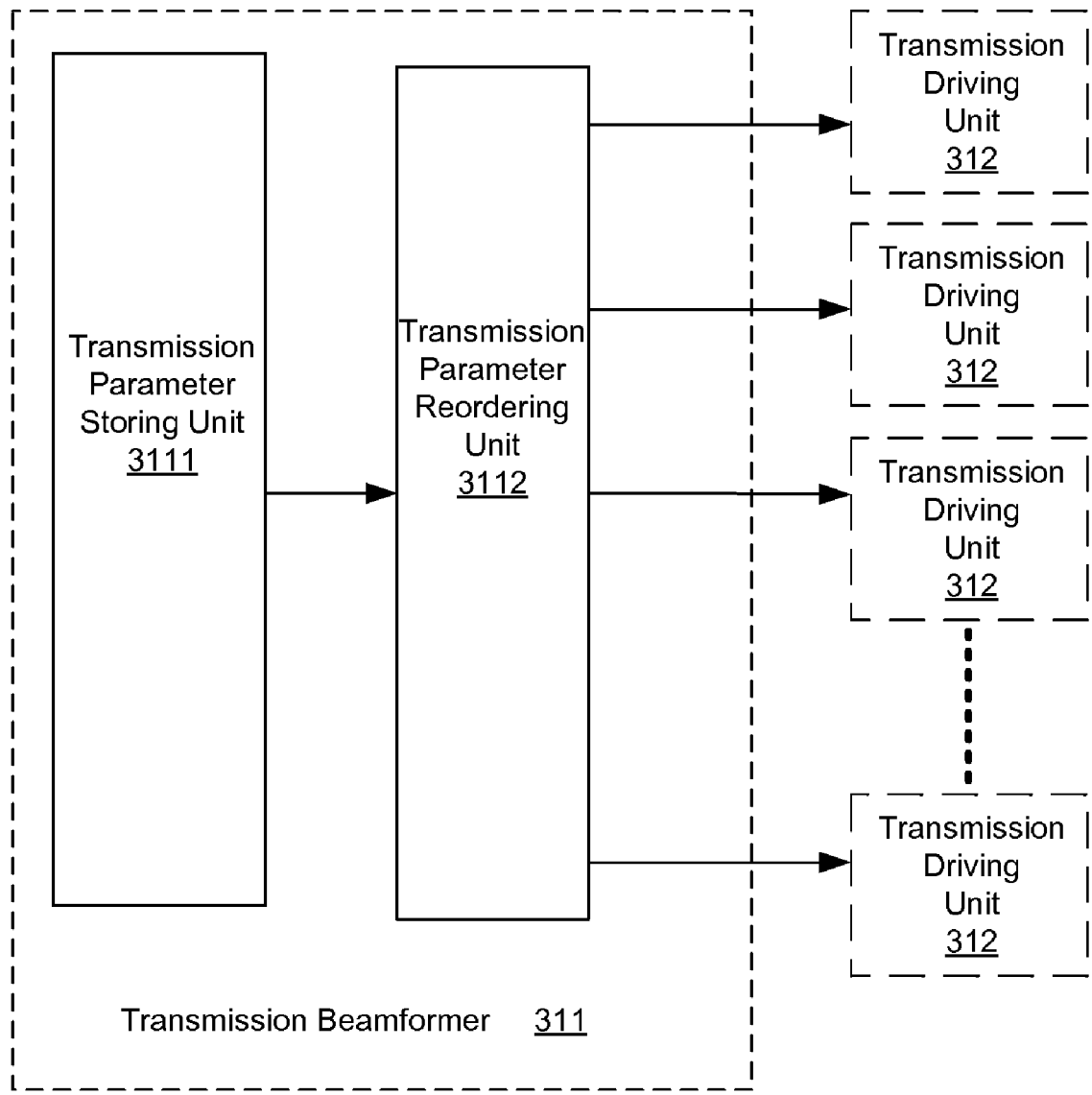
FIG. 3 is a block diagram showing the configuration of a transmission beamformer with digital reordering function in prior arts.
Figure 4:
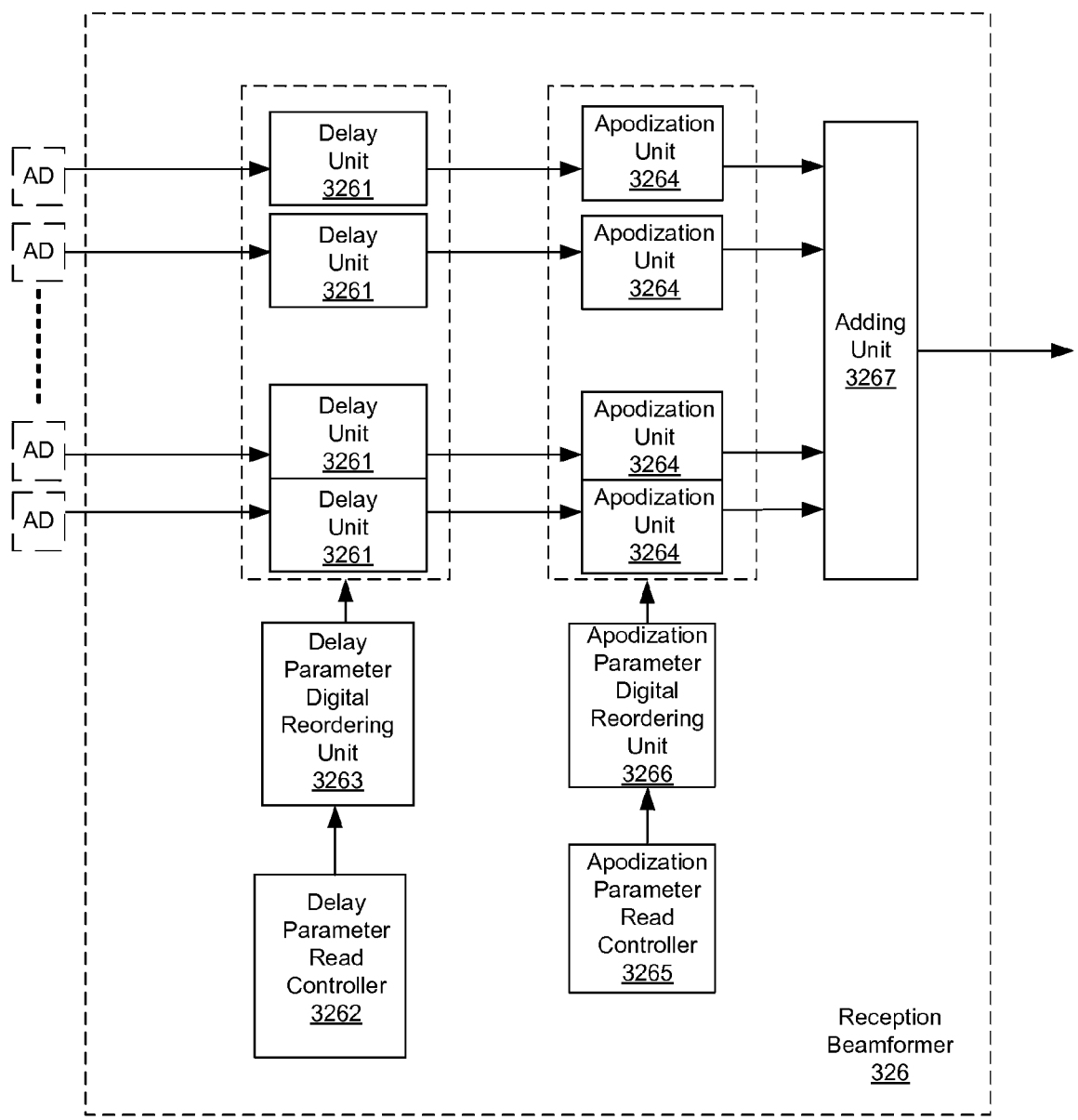
FIG. 4 is a block diagram showing the configuration of a reception beamformer with digital reordering function in prior arts.
Figure 5:
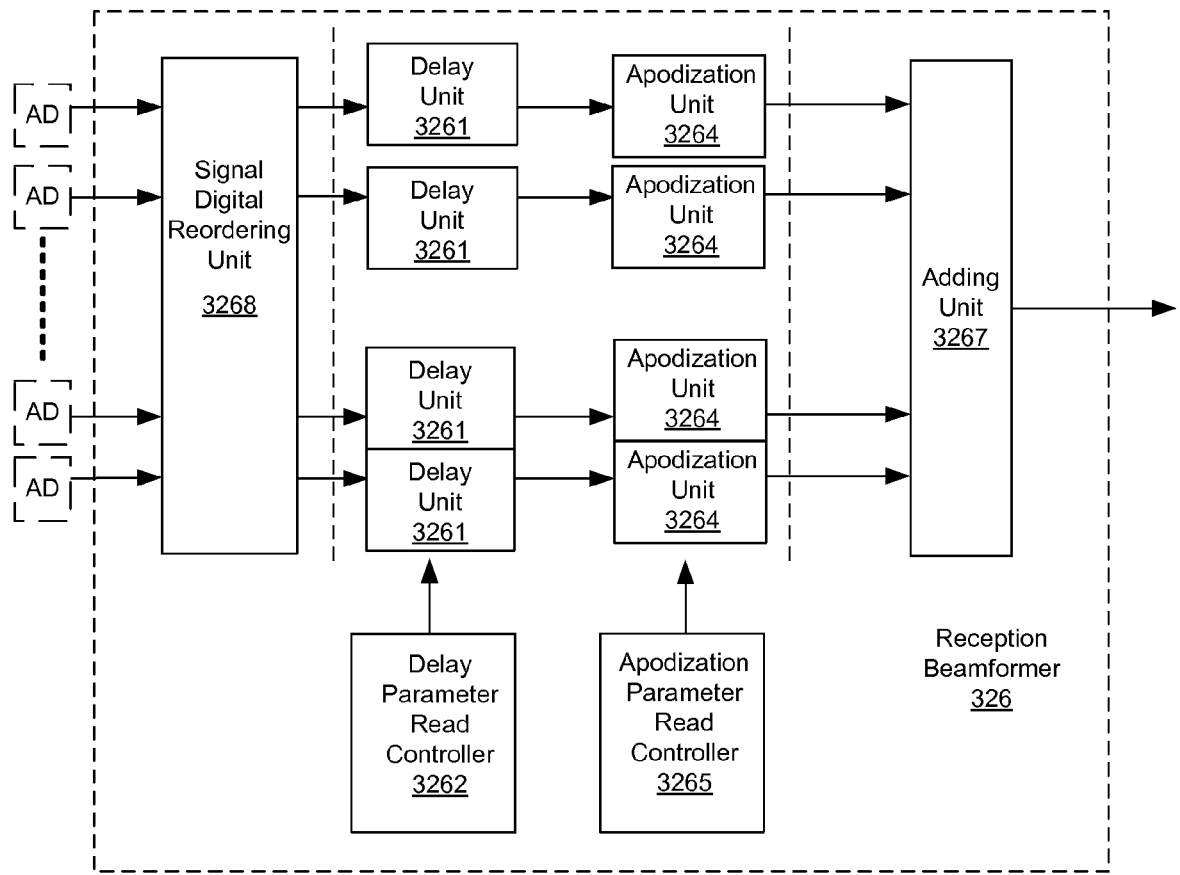
FIG. 5 is a block diagram showing the configuration of a reception beamformer with digital reordering function in prior arts.
Figure 6:
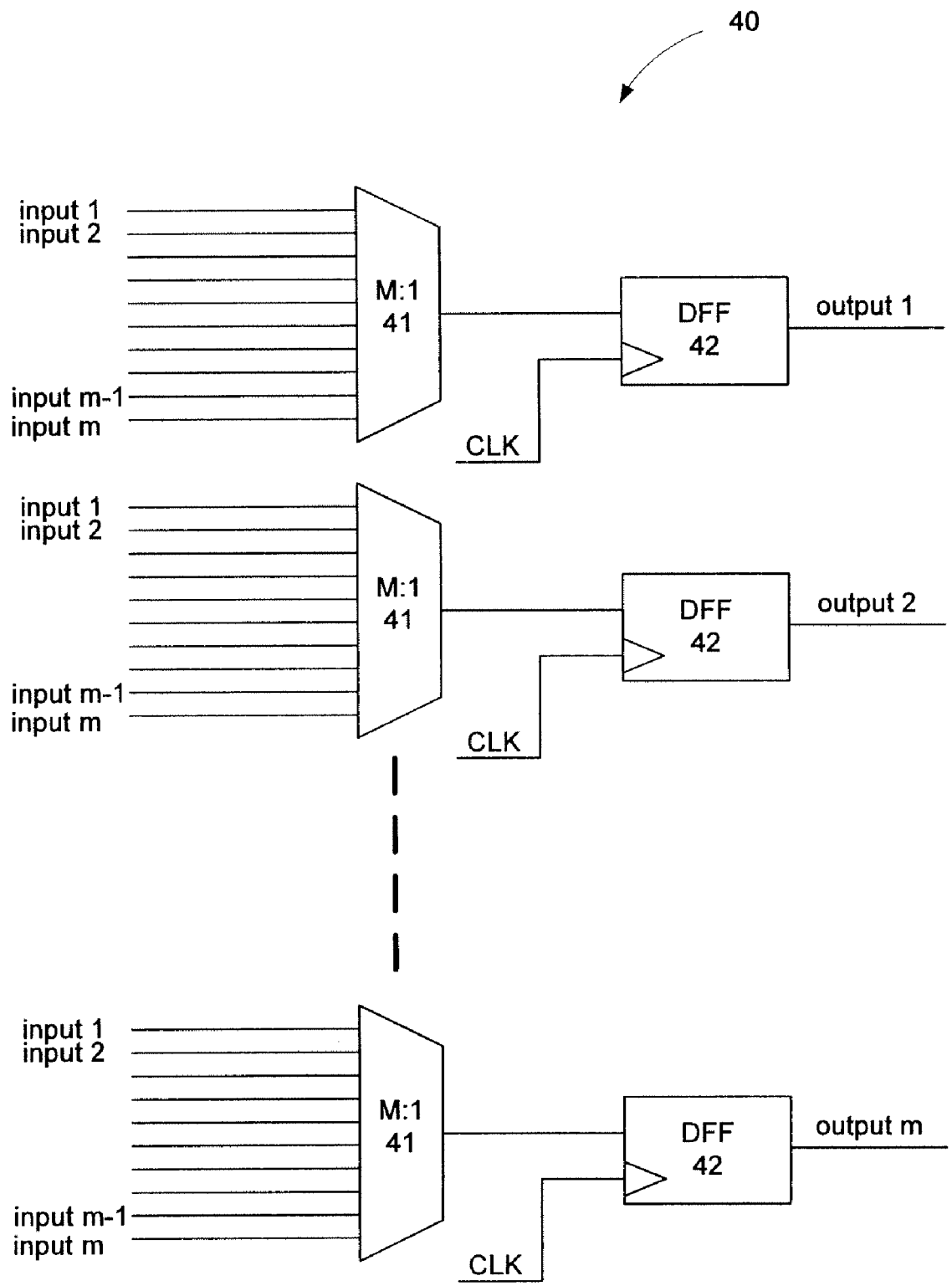
FIG. 6 is a diagram showing the digital reordering unit of FIGS. 3-5.
Figure 7:
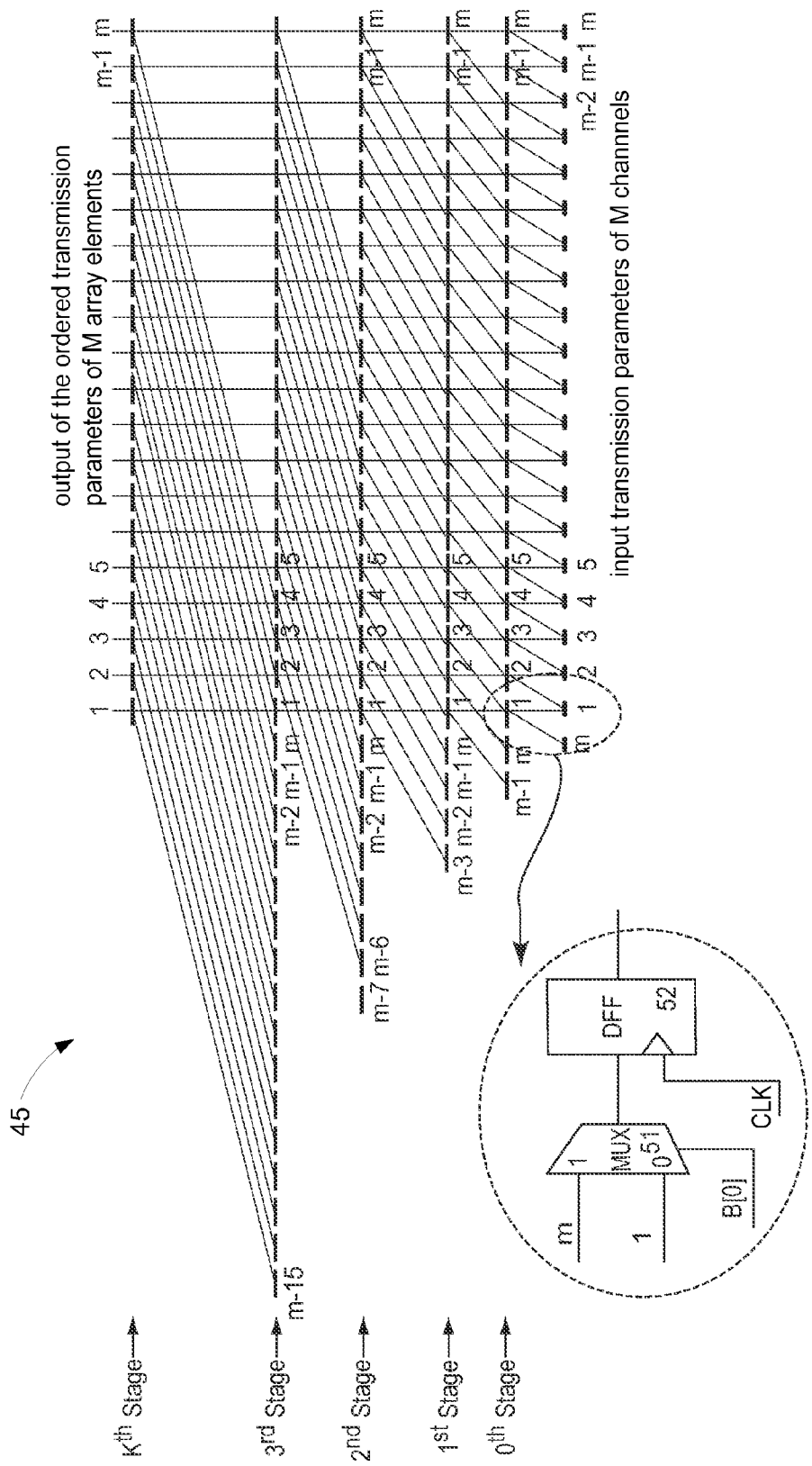
FIG. 7 is a diagram showing a digital reordering unit according to one embodiment of the invention.

FIG. 7 is a schematic diagram showing the configuration of a digital reordering unit 45 according to one embodiment of the invention. As shown in the figure, the digital reordering unit 45 comprises a plurality of 2:1 multiplexers 51 and a plurality of DFFs 52 coupled thereto correspondingly.

Figure 8:
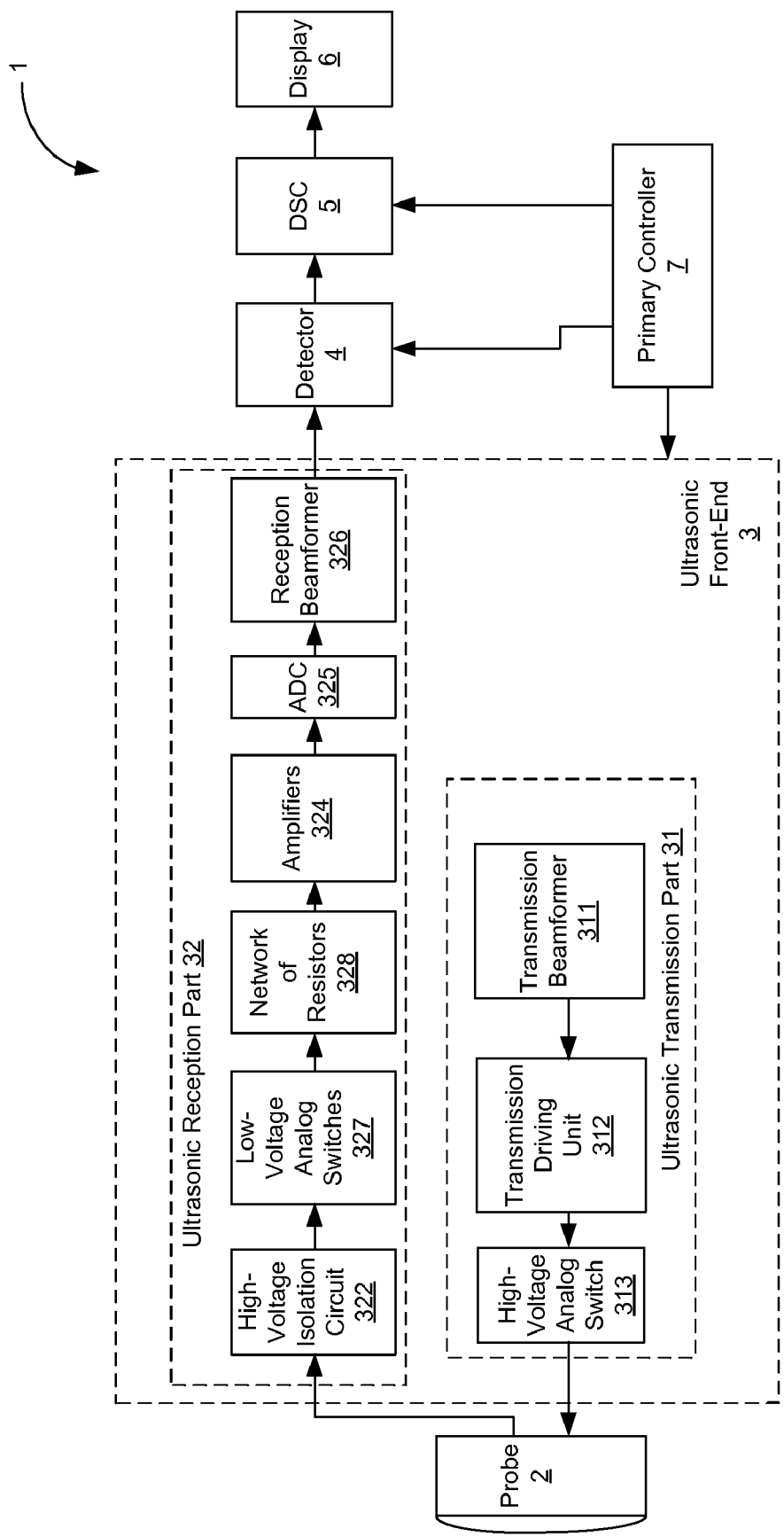
FIG. 8 is a block diagram showing the configuration of an ultrasonic front-end device in an ultrasonic system according to one embodiment of the invention.

FIG. 8 is a block diagram showing the configuration of an ultrasonic front-end device 3 in an ultrasonic diagnostic system 1 according to one embodiment of the invention. As shown in the figure, the ultrasonic system 1 mainly comprises a probe 2, an ultrasonic front-end 3, a detector 4, a DSC (Digital Scan Conversion) unit 5, a display 6 and a primary controller 7. The probe 2 has M array elements, where M is an integer larger than or equal to 1. The ultrasonic front-end 3 is equipped with an ultrasonic transmission part 31 comprising a transmission beamformer 311 and M transmission driving units 312, and has M transmission channels, and an ultrasonic reception part 32 comprises a high-voltage isolation circuit 322, RC amplifiers 324, RC ADCs 325 and a reception beamformer 326 electrically connected in said order and has RC reception channels, wherein RC [N, 2N, 3N ... p*N], N being an integer larger than or equal to 1. The ultrasonic front-end device characterizes in that M low-voltage analog switches 327 and a network of resistors 328 are serially connected between the high-voltage isolation circuit 322 and the RC amplifiers 324. The M low-voltage analog switches 327 are configured to electrically connect RC array elements of the M array elements in the probe 2 and the RC corresponding reception channels in the ultrasonic reception part 3 as the scan lines of the ultrasonic diagnostic system change. The network of resistors 328 is configured to connect the RC reception channels connected by the M low-voltage analog switches 327 and the RC amplifiers 324, as shown in FIG. 7 and FIG. 8. The network of resistors 328 is used to be compatible with a system having P types of reception channels, comprising M inputs IN[1, 2, 3, . . . , M] connected to the outputs of the low-voltage analog switches 326 and RC outputs OUT[1, 2, . . . , RC] connected to the inputs of the amplifiers 324. The structure of the network of resistors can be expressed by OUT[jj]=IN[jj+kk*RC], indicating that the output OUT[jj] and the input IN[jj+kk*RC] of the network of resistors 328 are connected through resistors, where 1≦jj≦RC, 0≦kk≦INT(M/RC), INT denotes taking the integer part. If jj+kk*RC>M, since such an Input does not exist, there is no resistor connecting the input and the output of the network of resistors 328. A digital reordering unit included in the reception beamformer 328 comprises a plurality of 2:1 multiplexers 51 and a plurality of DFFs 52 coupled thereto correspondingly. The ultrasonic front-end device 3 may be implemented on a PCB. For an ultrasonic diagnostic system 1 having a different number of reception channels, a different network of resistors 328 may be soldered on the PCB of the ultrasonic front-end device 3 and a corresponding number of amplifiers 324 and ADCs 325 may be soldered on the PCB. In this way, compatibility with an ultrasonic diagnostic system 1 having P types of and a different number (RC) of reception channels may be implemented by means of the same PCB.

The low-voltage analog switches 327 comprise a plurality of single-stage analog switches connected to the respective reception array elements in the probe through the isolation circuit 321 and are under the control of the primary controller 7. Assume the number of the reception array elements in the probe 2 is M, when the scan lines of the ultrasonic system 1 change, the corresponding reception channels change accordingly. By means of these analog switches 327, the ultrasonic system 1 may select RC out of the M array elements for reception and disable the other array elements not involved in the reception.

The connection between the network of resistors 328 and the low-voltage analog switches 327 and the amplifiers 324 is implemented through resistors, wherein based on the number of RC, the corresponding resistors in the network of resistors 328 are soldered with the low-voltage analog switches 327 and the amplifiers 324.

Figure 9:
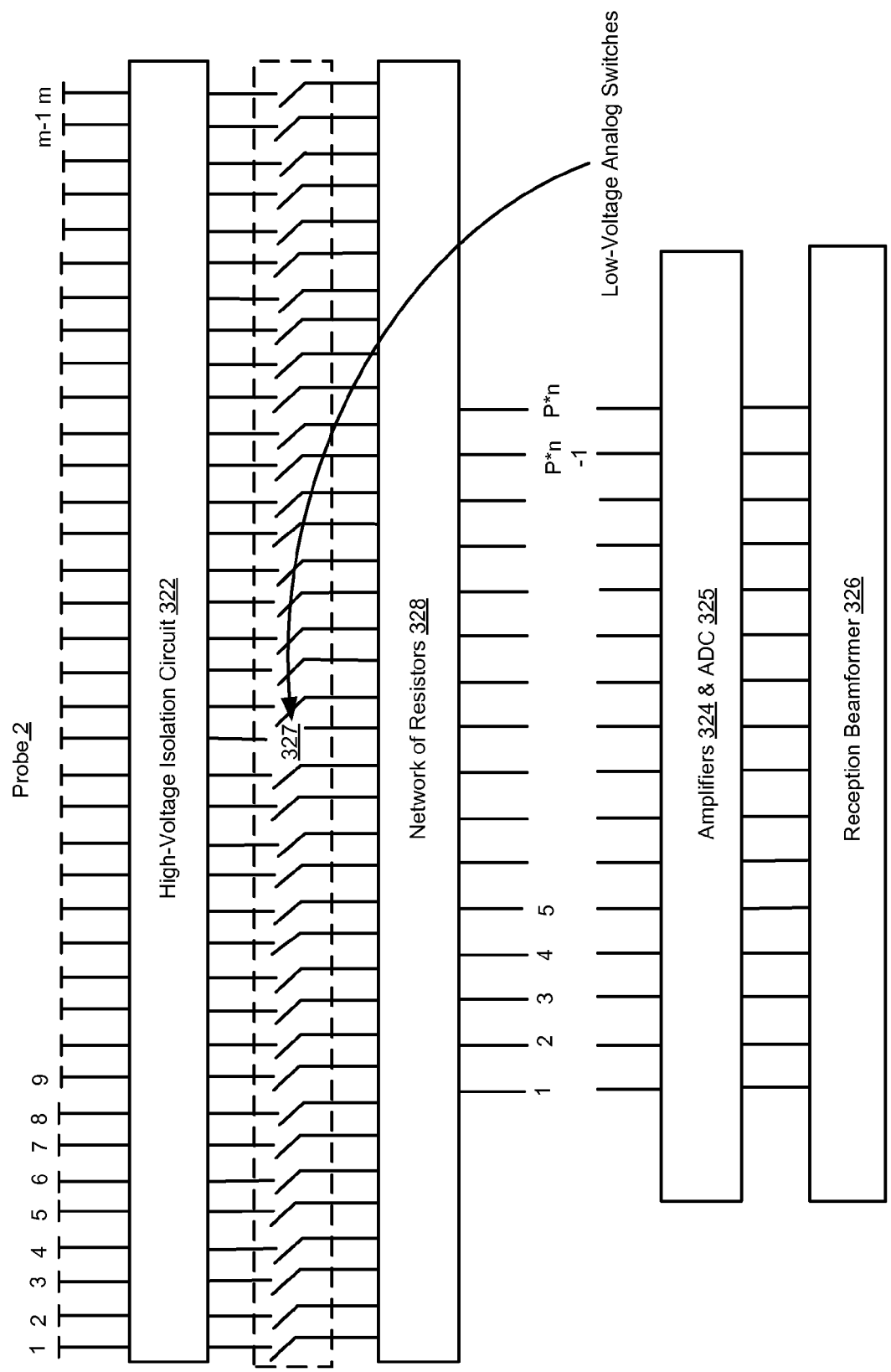
FIG. 9 is a diagram showing the configuration of an ultrasonic front-end reception unit in an ultrasonic system according to one embodiment of the invention.
Figure 10:
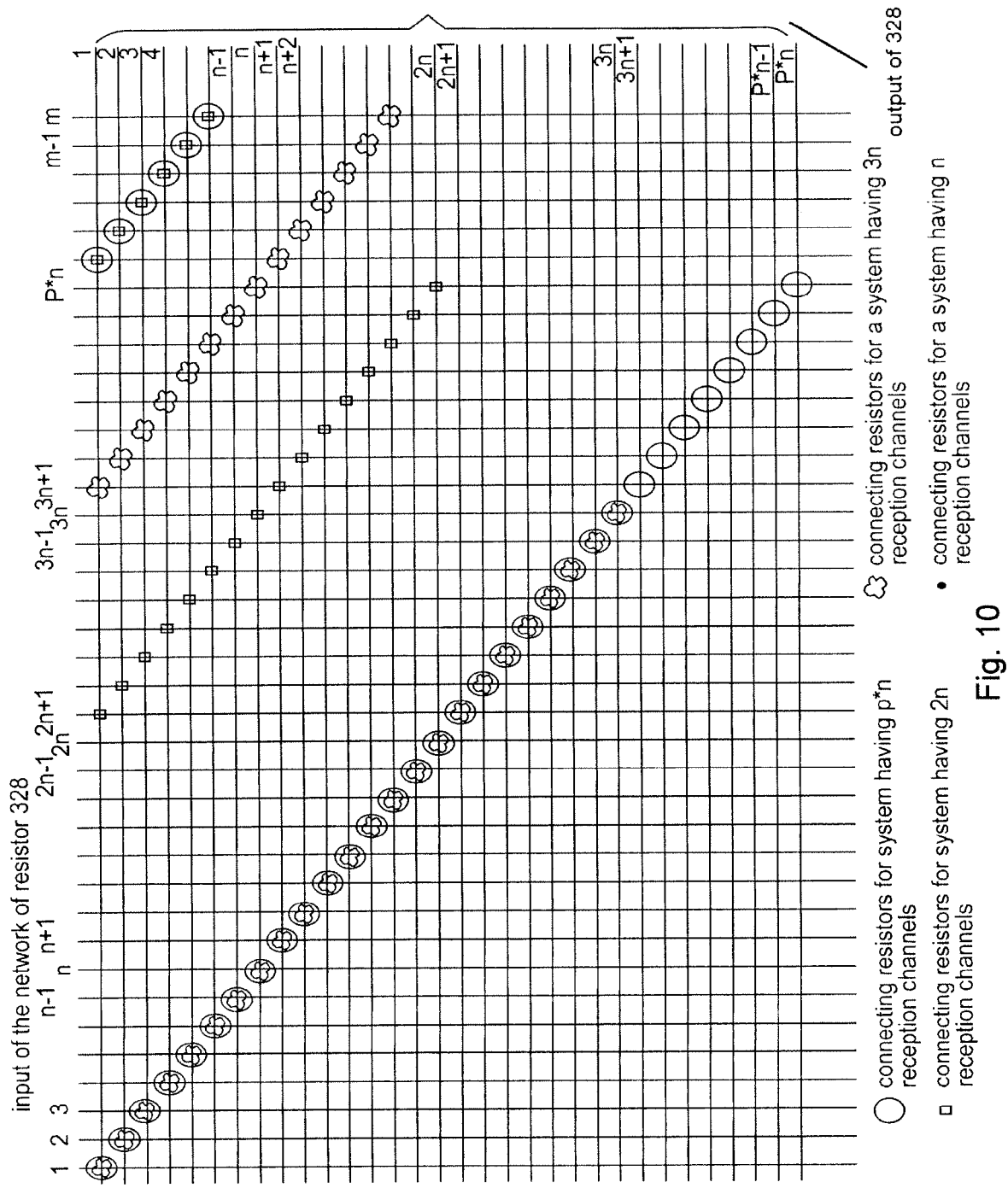
FIG. 10 shows the principle of the network of resistors in FIG. 8 and FIG. 9.

As shown in FIG. 9, the network of resistors 328 implements electrical connection between the selected array elements and the respective reception channels, accordingly it comprises M Inputs and RC outputs. When the maximum number of ultrasonic systems 1 that the ultrasonic front-end 2 can accommodate is P, the network of resistors 328 designed in accordance with the electrical connection relationship allows the ultrasonic system 1 to be compatible with an ultrasonic front-end having reception channel numbers of N, 2N, 3N, . . . , or P*N. The electrical connection may be implemented by resistors. As shown in FIG. 10, when RC=N, the outputs OUT[1, 2, 3, . . . , N] and the inputs IN[1, 2, 3 . . . , M] of the network of resistors 328 are electrically connected by resistors (the connections are shown by dots), while OUT[N+1, N+2, . . . , P*N] are not electrically connected. When RC=2N, the rectangular boxes represent the electrical connection between the outputs OUT[1, 2, 3, . . . , 2N] and the inputs IN[1, 2, 3, . . . , M], while OUT[2N+1, 2N+2, . . . , P*N] are not electrically connected. When RC=the maximum number of channels P*N, the circles represent the electrical connection between the outputs OUT[1, 2, 3, . . . , P*N] and the inputs IN[1, 2, 3, . . . , M]. In this way, in design of the same PCB, when the network of resistors 328 is designed to meet the requirement of an ultrasonic system having different number of reception channels, the union set of the connection relationships of the resistors in various compatible ultrasonic systems may be used to design the connection between the network of resistors, to remove redundancy and reduce the number of resistors. In this manner, for an ultrasonic system having N reception channels, the amplifiers 324 and the ADCs located after the network of resistors 328 need to have only N paths soldered. For an ultrasonic system having 2N reception channels, the amplifiers 324 and the ADCs located after the network of resistors 328 need to have only 2N paths soldered. For an ultrasonic system having P*N reception channels, the amplifiers 324 and the ADCs located after the network of resistors 328 need to have only P*N paths solder. Therefore, the compatibility with an ultrasonic diagnostic system having P types of reception channels may be achieved by using a single PCB, which Improves the compatibility of the ultrasonic front-end device 3 of the ultrasonic system 1 and reduces the cost of the ultrasonic system 1.

For the transmission beamformer 311 that performs digital reordering on the transmission parameters, its digital reordering unit comprises a plurality of delay parameter digital reordering units 3111. For the transmission beamformer that performs digital reordering on the transmission signals, its digital reordering unit is a single digital reordering unit 3118, comprising a plurality of 2:1 multiplexers 51 and a plurality of DFFs 52 coupled thereto correspondingly.

Figure 12:
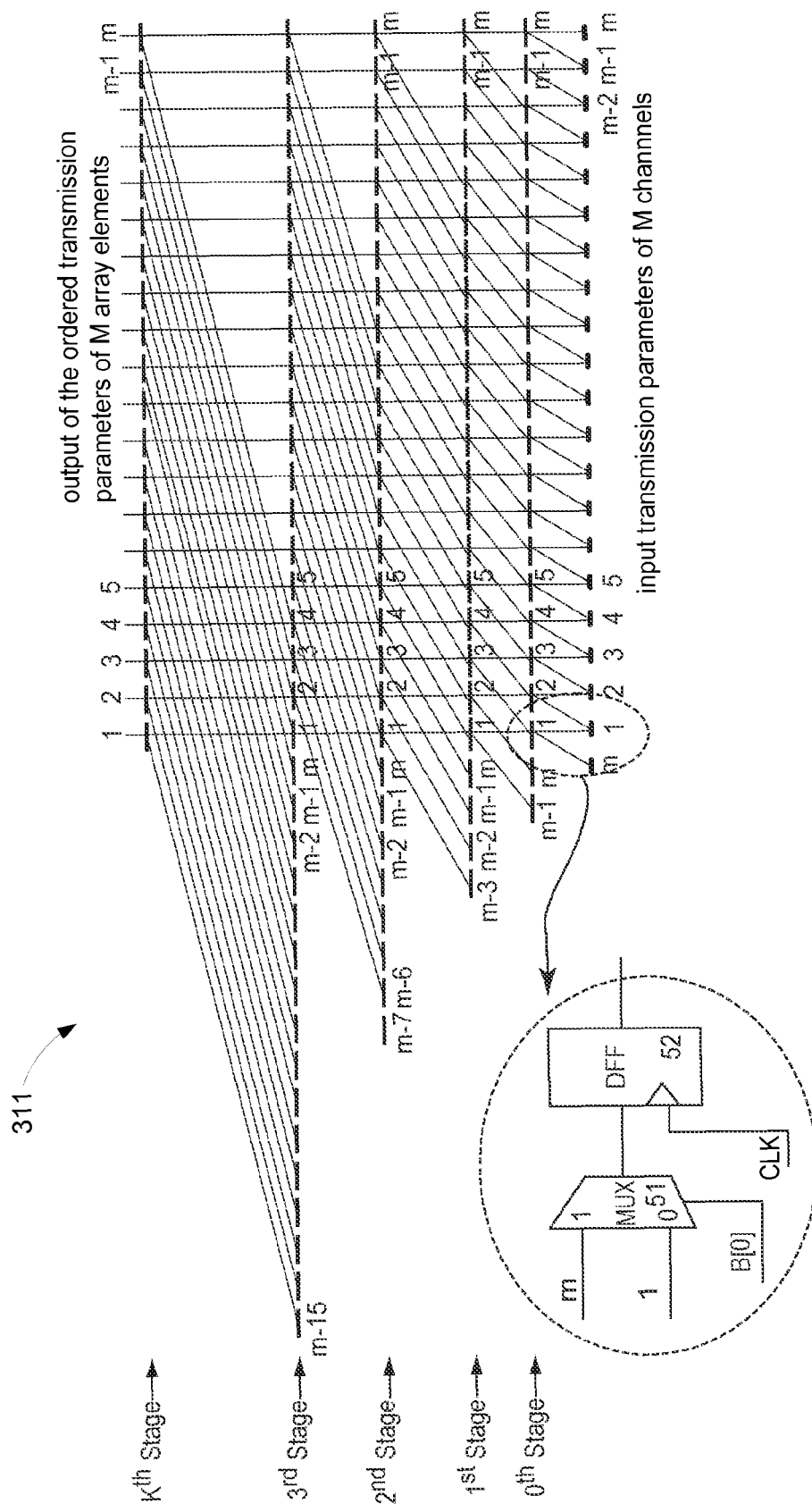
FIG. 12 is a diagram showing the digital reordering in the transmission beam forming according to the invention.

As shown in FIG. 12, the transmission beamformer 311 is configured to store a set of ordered transmission parameters corresponding to the respective transmission channels, to provide a binary control parameter B[K, K−1, K−2, 0] which varies as the scan lines of the ultrasonic system change, for controlling an array of 2:1 multiplexers 51 to convert the ordered transmission parameters into parameters for the current transmission channels. The array of 2:1 multiplexers 51 comprises a plurality of stages each having M 2:1 multiplexers. Each bit of the parameter controls M 2:1 multiplexers at a corresponding stage, wherein $2^{K+1} \geq M$ and K is an integer larger than or equal to 0. The inputs at the $0^{th}$ stage are the transmission parameters for the M transmission channels. Each bit of the parameter B is used to control M 2:1 multiplexers at a stage: if the bit is 0, the data from the "0" inputs of the 2:1 multiplexers are output, otherwise, the data from the "1" inputs of the 2:1 multiplexers are output. The signals on the "1" inputs of the array of 2:1 multiplexers are shifted $2^K$ units rightward, for example, the signals on the "1" inputs of the multiplexers at the $0^{th}$ stage are shifted 1 unit rightward, the signals on the "1" inputs of the multiplexers at the $1^{st}$ stage are shifted 2 units rightward, the signals on the "1" inputs of the multiplexers at the $2^{nd}$ stage are shifted 4 units rightward, signals on the "1" the inputs of the multiplexers at the $3^{rd}$ stage are shifted 8 units rightward, . . . , and the signals on the "1" inputs of the multiplexers at the $K^{th}$ stage are shifted $2^K$ units rightward. The shift is in accordance with the binary coding format and the outputs from the 2:1 multiplexers at the last stage are M digitally reordered transmission parameters.

The reception beamformer 326 may be classified into two types. A reception beamformer 326 for performing digital reordering on the received parameters, comprises delay units 3261, a delay parameter read controller 3262, a delay parameter digital reordering unit 3263, apodization units 3264, an apodization parameter read controller 3266, an apodization parameter digital reordering unit 3266 and an adding unit 3287, The reception beamformer 326 delays, apodises, reorders and adds the signals received from the ADCs 325, to synthesize the received beam signals. The delay parameter digital reordering unit 3263 and the apodization parameter digital reordering unit 3266 each comprises multiple stages each of which has P"N 2:1 multiplexers 51 followed with P*N corresponding DFFs 52. A reception beamformer 326 for performing digital reordering on the received signals comprises a digital reordering unit 3288, delay units 3261, a delay parameter read controller 3282, apodization unite 3284, an apodization parameter read controller 3285 and an adding unit 3267. The reception beamformer 328 reorders, delays, apodises and adds the signals received from the ADC 325, to synthesize the received beam signals. The signal digital reordering unit 3288 comprises multiple stages each having P*N 2:1 multiplexers 51 followed by the corresponding DFFs 52.

Figure 13:
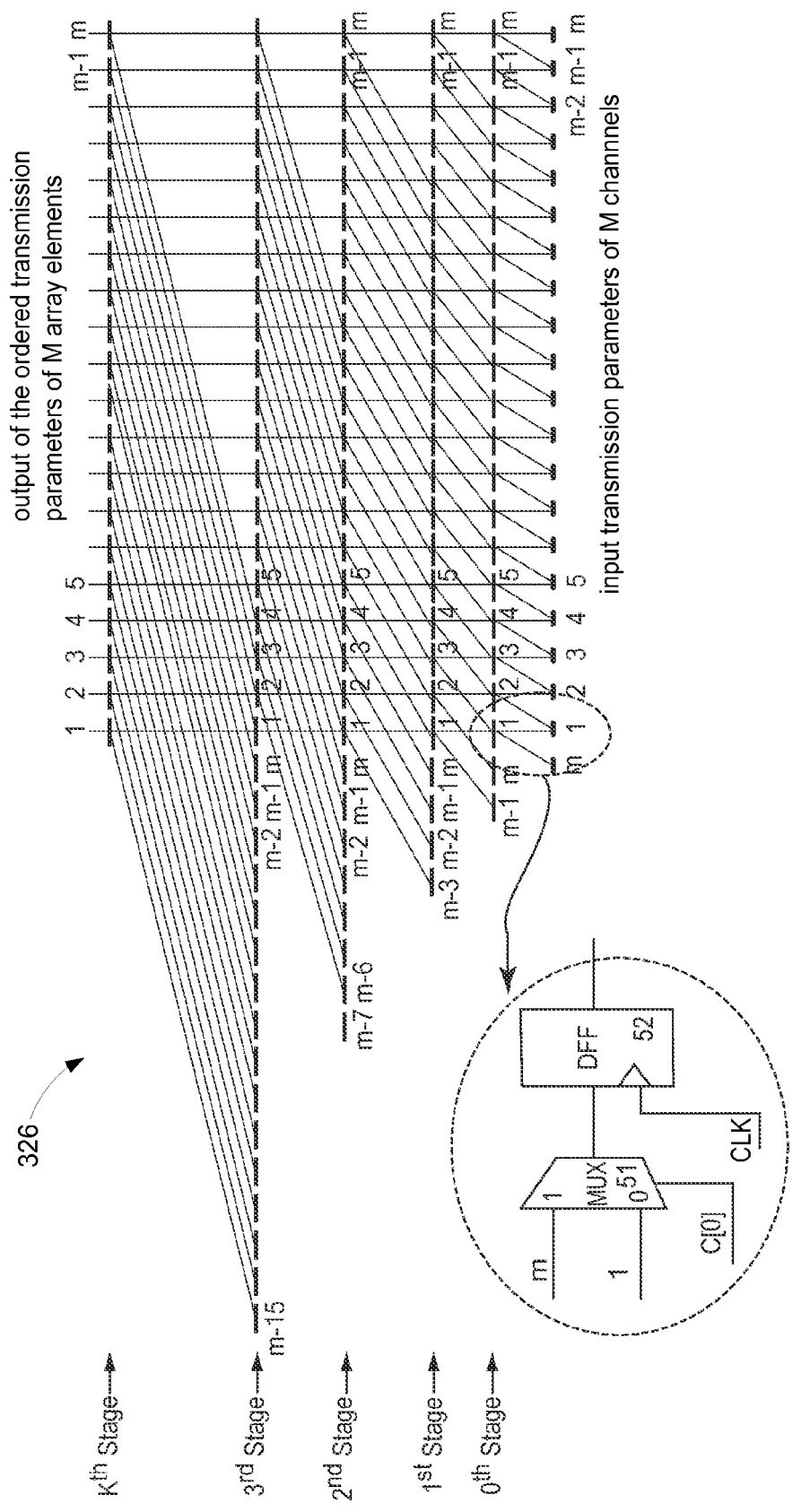
FIG. 13 is a diagram showing the digital reordering in the reception beam forming according to the invention.

As shown in FIG. 13, when digitally reordering the reception parameters, the reception beamformer 326 is configured to store a set of ordered reception parameters corresponding to the reception channels. The parameter controls an array of 2:1 multiplexers to convert the ordered reception parameters into parameters for the current reception channels. The array of 2:1 multiplexers comprises multiple stages, each of which has P*N 2:1 multiplexers 51. Each bit of the parameter is used to control P*N 2:1 multiplexers 51 at a corresponding stage, where $2^{K+1} \geq P*N$, and K is an integer larger than or equal to 0. The inputs of the P*N 2:1 multiplexers 51 at the $0^{th}$ stage is set to the ordered reception parameters for the corresponding reception channels. Each bit of the parameter C is used to control 2:1 multiplexers 51 at a stage: if the bit is 0, the data from the "0" inputs of the 2:1 multiplexers are output, otherwise, the data from the "1" inputs of the 2:1 multiplexers are output. The signals on the "1" inputs of the whole array are shifted rightward, the multiplexers at the $0^{th}$ stage are shifted 1 unit rightward, the signals on the "1" inputs of the multiplexers at the $1^{st}$ stage are shifted 2 units rightward, the signals on the "1" inputs of the multiplexers at the $2^{nd}$ stage are shifted 4 units rightward, the signals on the "1" inputs of the multiplexers at the $3^{rd}$ stage are shifted 8 units rightward, . . . , and the signals on the "1" inputs of the multiplexers at the $K^{th}$ stage are shifted $2^K$ units rightward. The shift complies with the binary coding format and the outputs from the 2:1 multiplexers 51 at the last stage are P*N digitally reordered parameters.

When digitally reordering the received signals, signals from the ADCs 325 are received at the input of the reception beamformer 328, which performs digital reordering on the received signals in a manner similar to digital reordering on the reception parameters. The reception beamformer 328 outputs ordered channel signals.

Figure 11:
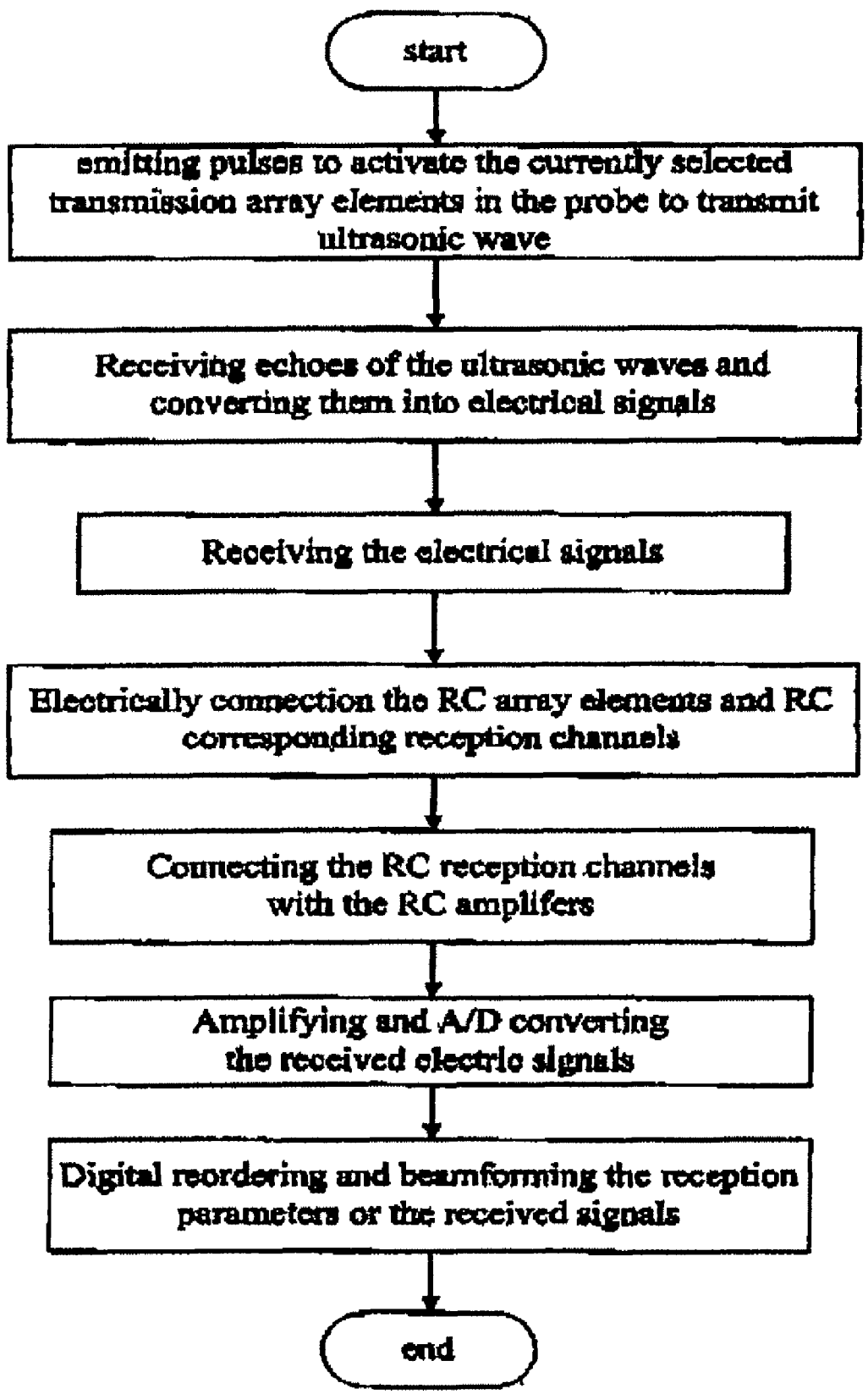
FIG. 11 is a flowchart showing a method of using the compatibility of an ultrasonic front-end device in an ultrasonic system according to one embodiment of the invention.

FIG. 11 is a flowchart showing a method of using an ultrasonic front-end device 3 in an ultrasonic system 1 according to one embodiment of the invention. As shown in FIG. 8, the ultrasonic front-end device 3 is connected between a probe 2 and a detector 4 of the ultrasonic system 1 and controlled by a primary controller 7 of the ultrasonic system. The probe 2 has M array elements. The ultrasonic front-end device 3 has an ultrasonic transmission part 31 and an ultrasonic reception part 32, wherein the ultrasonic transmission part 31 comprises a transmission beamformer 311 and a transmission driving unit 312, while the ultrasonic reception part 32 has RC reception channels and comprises a high-voltage isolation circuit 322, RC amplifiers 324, RC ADCs 325 and a beamformer 326 electrically connected in said order, where RC=[N, 2N, 3N . . . p*N], N being an integer larger than or equal to 1. The ultrasonic front-end device characterizes in that M low-voltage analog switches 327 and a network of resistors 318 are serially connected between the high-voltage isolation circuit 322 and the RC amplifiers 324, wherein the M low-voltage analog switches 327 is configured to electrically connect RC array elements of the M array elements in the probe 2 and RC respective reception channels In the ultrasonic reception part 3 as the scan lines of the ultrasonic system change. The network of resistors 328 is configured to connect the RC reception channels connected by the M low-voltage analog switches 327 and the RC amplifiers 324. The network of resistors 328 comprises M inputs IN[1, 2, 3, . . . , M] connected to the outputs of the low-voltage analog switches 327 and RC outputs OUT[1, 2, . . . , RC] connected to the inputs of the amplifiers 324. The structure of the network of resistors can be expressed by OUT[jj]=IN[jj+kk*RC], indicating that the output OUT[jj] and the input IN[jj+kk*RC] of the network of resistors 328 are connected through resistors, where 1≦jj≦RC, 0≦kk≦INT(M/RC), INT denotes taking the integer part. If j+kk*RC>M, since such an input does not exist, there is no resistor connecting the input and the output of the network of resistors 328. A digital reordering unit included in the reception beamformer 328 comprises a plurality of 2:1 multiplexers 51 having a "0" Input and a "1" input and the DFFs 62 coupled thereto correspondingly, the method comprising the steps of:

1. emitting pulses by the ultrasonic transmission part 31 with transmission parameters, to activate the currently selected transmission array elements in the probe 2 of the ultrasonic system 2 to transmit ultrasonic waves;

2. receiving echoes of the ultrasonic waves and converting them into electric signals by the currently selected reception array elements in the probe 2;

3. receiving electric signals from the probe by the high-voltage isolation circuit;

4. electrically connecting, by the M low-voltage analog switches 321 in the ultrasonic reception part 32, RC array elements of the M array elements in the probe 2 and RC corresponding reception channels in the ultrasonic reception part 32 as the scan lines of the ultrasonic system 1 change;

5. connecting, by the network of resistors 328, the RC reception channels connected by the M low-voltage analog switches 327 with the RC amplifiers 324;

6. amplifying and AD converting the received electric signals by the amplifiers 324 and the ADCs 326 in the ultrasonic reception part 32; and 7. digital reordering and beamforming the reception parameters or the received signals by the beamformer 326 in the ultrasonic reception part 32.

Step 1 comprises the substeps of: (1a) setting and storing a set of ordered transmission parameters corresponding to the M transmission channels, by the transmission beamformer 311 in the ultrasonic transmission part 31; and (1b) providing, by the transmission beamformer 311, a binary control parameter B[K, K−1, K−2, . . . , 0] which varies as the scan lines of the ultrasonic system change. The parameter controls an array of 2:1 multiplexers to convert the ordered transmission parameters into parameters for the current transmission channels. The array of 2:1 multiplexers comprises a plurality of stages each having M 2:1 multiplexers 51. Each bit of the parameter controls M 2:1 multiplexers 51 at a corresponding stage, wherein $2^{K+1} \geq M$, K is an integer larger than or equal to 0. The inputs at the $0^{th}$ stage are the ordered transmission parameters for the M transmission channels. Each bit of the parameter B is used to control M 2:1 multiplexers 51 at a stage: if the bit is 0, the data from the "0" inputs of the 2:1 multiplexers 51 are output, otherwise, the data from the "1" inputs of the 2:1 multiplexers 51 are output. The signals on the "1" inputs of the array of 2:1 multiplexers are shifted $2^K$ units rightward, for example, the signals on the inputs of the multiplexers 51 at the $0^{th}$ stage are shifted 1 unit rightward, the signals on the inputs of the multiplexers 51 at the $1^{st}$ stage are shifted 2 units rightward, the signals on the inputs of the multiplexers 51 at the $2^{nd}$ stage are shifted 4 units rightward, the signals on the inputs of the multiplexers 51 at the $3^{rd}$ stage are shifted 8 units rightward, . . . , and the signals on the inputs of the multiplexers 51 at the $K^{th}$ stage are shifted $2^K$ units rightward. The shift complies with the binary coding format and the outputs from the 2:1 multiplexers at the last stage are M digitally reordered transmission parameters.

There are two types of digital reordering at the step 7: first, conduct digital reordering on the received signals while no digital reordering on the reception parameters; second, conduct digital reordering on the reception parameters while no digital reordering on the received signals.

For the reception parameters, the digital reordering and beam forming at the step 7 comprise the substeps of: (7a) setting and storing a set of ordered reception parameters corresponding to the reception channels, by the reception beamformer 326 in the ultrasonic reception part 32; and (7b) providing, by the reception beamformer 326, a binary control parameter C[K, K−1, K−2, . . . , 0] which varies as the scan lines of the ultrasonic system 1 change. The control parameter controls an array of 2:1 multiplexers to convert the ordered reception parameters into parameters for the current reception channels. The array of 2:1 multiplexers comprises multiple stages, each of which has P*N 2:1 multiplexers 51. Each bit of the parameter controls P*N 2:1 multiplexers at a corresponding stage, where $2^{K+1} \geq P*N$ and K is an integer larger than or equal to 0, wherein the inputs of the P*N 2:1 multiplexers 51 at the $0^{th}$ stage are the reception parameters for the corresponding reception channels. Each bit of the parameter C is used to control 2:1 multiplexers 51 at a corresponding stage: if the bit is 0, the data from the "0" inputs of the 2:1 multiplexers 51 are output, otherwise, the data from the "1" inputs of the 2:1 multiplexers 51 are output. The signals on the "1" inputs of the whole array of 2:1 multiplexers 51 are shifted $2^K$ units rightward, for example, the signals on the "1" inputs of the multiplexers 51 at the $0^{th}$ stage are shifted 1 unit rightward, the signals on the "1" inputs of the multiplexers 51 at the $1^{st}$ stage are shifted 2 units rightward, the signals on the "1" inputs of the multiplexers 51 at the $2^{nd}$ stage are shifted 4 units rightward, . . . , and the signals on the "1" inputs of the multiplexers 51 at the $K^{th}$ stage are shifted $2^K$ units rightward.

For the received signals, the digital reordering and beam forming at the step 7 comprises the substeps of: providing, by the reception beamformer 326, a binary control parameter C[K, K−1, K−2, . . . , 0] which varies as the scan lines of the ultrasonic system 1 change. The control parameter controls an array of 2:1 multiplexers, the array of 2:1 multiplexers including k+1 stages, each stage having P*N 2:1 multiplexers 51, where $2^{K+1} \geq P*N$, and K is an integer larger than or equal to 1. Signals from the ADCs are received at the inputs of the P*N 2:1 multiplexers 51 at the $0^{th}$ stage. Each bit of the parameter C is used to control M 2:1 multiplexers 51 at a stage: if the bit is 0, the data from the "0" inputs of the 2:1 multiplexers 51 are output, otherwise, the data from the "1" inputs of the 2:1 multiplexers 51 are output. The signals on the "1" inputs of the array of 2:1 multiplexers 51 are shifted $2^K$ units rightward, for example, the signals on the "1" inputs of the multiplexers 51 at the $0^{th}$ stage are shifted 1 unit rightward, the signals on the "1" inputs of the multiplexers 51 at the $1^{st}$ stage are shifted 2 units rightward, the signals on the "1" inputs of the multiplexers 51 at the $2^{nd}$ stage are shifted 4 units rightward, the signals on the "1" inputs of the multiplexers 51 at the $3^{rd}$ stage are shifted 8 units rightward, . . . , and the signals on the "1" inputs of the multiplexers 51 at the $K^{th}$ stage are shifted $2^K$ units rightward. The shift complies with the binary coding format and the outputs from the 2:1 multiplexers 51 at the last stage are P*N of digitally reordered signals.

The above-mentioned various solutions provide compatibility for an ultrasonic front-end device in an ultrasonic system and reduce the cost of the ultrasonic system. The digital reordering unit for use in the ultrasonic front-end has advantages in being highly real time and less consumption of hardware resources.

The inventive method is tested in experiments, leading to implementation of a high-speed and real-time ultrasonic system as well as improvement in the compatibility for the ultrasonic front-end of the ultrasonic system and cost saving for the ultrasonic system.

Preferred embodiments of the present invention have thus been shown and described. It would be apparent to one of ordinary skill in the art, however, that various variations, alternatives and alterations may be made to the embodiments herein disclosed without departing from the spirit or scope of the invention.

What is claimed is:

1. A digital reordering unit of an ultrasonic system for use in an ultrasonic front-end device, the digital reordering unit receiving a set of ordered parameters that are arranged according to respective channels of the ultrasonic front-end device, the ordered parameters used for processing electrical signals corresponding to the respective channels, comprising:
   a plurality of stages, each stage comprising a plurality of multiplexers and a plurality of D-type flip-flops (DFFs) coupled thereto correspondingly;
   wherein inputs of a first stage receive the set of ordered parameters, and
   wherein outputs of the first stage are provided to inputs of a second stage to selectively reorder the ordered parameters based on changes in scan lines of the ultrasonic system;
   wherein the set of ordered parameters comprises a set of ordered transmission parameters, wherein the ultrasonic front-end is connected between a probe and a detector and includes a transmission beamformer configured to store the set of transmission parameters corresponding to respective transmission channels, wherein the reordered parameters comprise the transmission parameters, wherein the probe comprises M number of array elements where M is an integer larger than or equal to 1, and wherein each stage comprises M number of 2:1 multiplexers followed with respective DFFs; and
   wherein the transmission beamformer is configured to provide a control parameter which varies as the scan lines of the ultrasonic system change, wherein each bit of the control parameter controls M 2:1 multiplexers at a corresponding stage, wherein inputs at the first stage comprise the transmission parameters for M transmission channels.

2. The digital reordering unit of claim 1, wherein the control parameter comprises a binary control parameter B[K, K−1, K−2, . . . , 0], where $2^{K+1} \geq M$, K being an integer larger than or equal to zero and corresponding to a respective stage.

3. The digital reordering unit of claim 2, wherein each 2:1 multiplexer comprises a first input and a second input, wherein signals on the second inputs of the 2:1 multiplexers are shifted $2^K$ units laterally from one stage to the next, the shift complying with a binary coding format, and wherein output from the 2:1 multiplexers at a last stage comprise M digitally reordered transmission parameters.

4. The digital reordering unit of claim 1, wherein the set of ordered parameters comprises a set of reception parameters, wherein the ultrasonic front-end is connected between a probe and a detector and includes a reception beamformer configured to store the set of reception parameters corresponding to respective RC number of reception channels, wherein the reordered parameters comprise the reception parameters, wherein the ultrasonic front-end device is compatible with P types of reception channels where P is an integer larger than or equal to 1, wherein RC=[N, 2N, 3N, . . . , P*N] where N is an integer larger than or equal to 1, and wherein each stage comprises P*N number of 2:1 multiplexers followed with respective DFFs.

5. The digital reordering unit of claim 4, wherein the reception parameters are selected from the group comprising delay parameters and apodization parameters.

6. The digital reordering unit of claim 4, wherein the reception beamformer is configured to provide a binary control parameter C[K, K−1, K−2, . . . , 0] which varies as the scan lines of the ultrasonic system change, wherein each bit of the binary control parameter C[K, K−1, K−2, . . . , 0] controls P*N 2:1 multiplexers at a corresponding stage, wherein the digital reordering unit comprises K+1 stages, $2^{K+1} \geq P*N$, K being an integer larger than or equal to zero, and wherein inputs at the first stage comprise the reception parameters for the RC reception channels.

7. The digital reordering unit of claim 6, wherein each 2:1 multiplexer comprises a first input and a second input, wherein signals on the second inputs of the 2:1 multiplexers are shifted $2^K$ units laterally from one stage to the next, the shift complying with a binary coding format, and wherein output from the 2:1 multiplexers at a last stage comprise P*N digitally reordered reception parameters.

8. An ultrasonic front-end device, comprising:
   an ultrasonic transmission part for emitting pulses to activate currently selected transmission array elements in a probe of an ultrasonic system to transmit ultrasonic waves; and
   an ultrasonic reception part for receiving electric signals from currently selected reception array elements in the probe, the received electric signals having an order based on the currently selected reception array elements, the received electric signals corresponding to echoes of the transmitted ultrasonic waves, the ultrasonic reception part comprising a first digital reordering unit for reordering the received electrical signals, the first digital reordering unit comprising:
   a plurality of stages, each stage comprising a plurality of multiplexers and a plurality of D-type flip-flops (DFFs) coupled thereto correspondingly;
   wherein the received electric signals are applied to inputs of a first stage according to the order based on the currently selected reception array elements, and
   wherein outputs of the first stage are provided to inputs of a second stage to selectively reorder the received electrical signals based on changes in scan lines of the ultrasonic system;
   wherein the ultrasonic reception part further comprises RC number of reception channels, wherein the ultrasonic front-end device is compatible with P types of reception channels where P is an integer larger than or equal to 1, wherein RC=[N, 2N, 3N, . . . , P*N] where N is an integer larger than or equal to 1, and wherein each stage of the first digital reordering unit comprises P*N number of 2:1 multiplexers followed with respective DFFs; and
   wherein the ultrasonic reception part further comprises a reception beamformer configured to provide a binary control parameter C[K, K−1, K−2, . . . , 0] which varies as the scan lines of the ultrasonic system change, wherein each bit of the binary control parameter C[K, K−1, K−2, . . . , 0] controls P*N 2:1 multiplexers at a corresponding stage of the first digital reordering unit, wherein the first digital reordering unit comprises K+1 stages, $2^{K+1} >= P*N$, K being an integer larger than or equal to zero, and wherein inputs at the first stage comprise the received electrical signals for the RC reception channels.

9. The ultrasonic front-end of claim 8, wherein each 2:1 multiplexer comprises a first input and a second input, wherein signals on the second inputs of the 2:1 multiplexers are shifted $2^K$ units laterally from one stage to the next, the shift complying with a binary coding format, and wherein output from the 2:1 multiplexers at a last stage comprise P*N digitally reordered electrical signals.

10. The ultrasonic front-end of claim 8, wherein the ultrasonic reception part further comprises:
   M number of high-voltage isolation circuits, wherein M represents a number of array elements in the probe of the ultrasonic system; and
   M number of low-voltage analog switches electrically connected to the M high-voltage isolation circuits, the M low-voltage analog switches configured to connect RC number of the array elements in the probe to RC number of respective reception channels in the ultrasonic reception part as the scan lines of the ultrasonic diagnostic system change.

11. The ultrasonic front-end of claim 10, wherein the ultrasonic reception part further comprises:
   a network of resistors electrically connected to the M low-voltage analog switches;
   RC number of amplifiers electrically connected to the network of resistors, the network of resistors comprising M number of inputs IN[1, 2, 3, . . . , M] connected to respective outputs of the M low-voltage analog switches and RC number of outputs OUT[1, 2, . . . , RC] connected to respective inputs of the RC amplifiers;
   RC number of analog-to-digital converters (ADCs) electrically connected to the RC amplifiers; and
   a reception beamformer electrically connected to the RC ADCs, the reception beamformer comprising the first digital reordering unit and configured for beamforming the reordered electrical signals.

12. The ultrasonic front-end of claim 11, wherein a structure of the network of resistors can be expressed by the following formula:
   OUT[jj]=IN[jj+kk*RC], indicating that the output OUT [jj] and the input IN[jj+kk*RC] of the network of resistors are connected through resistors, where 1<=jj<=RC, 0<=kk<=INT(M/RC), INT denotes taking the integer part, if jj+kk*RC>M.

13. The ultrasonic front-end of claim 8, wherein the ultrasonic reception part further comprises:
   a reception beamformer configured to store a set of ordered reception parameters that are arranged according to respective reception channels of an RC number of reception channels, the set of ordered parameters comprising ordered delay parameters and ordered apodization parameters;
   one or more second digital reordering units for reordering delay parameters of the reception parameters; and
   one or more third digital reordering units for reordering the ordered apodization parameters of the reception parameters;
   wherein the one or more second digital reordering units and the one or more third digital reordering units each comprise:
      a plurality of stages, each stage comprising a plurality of multiplexers and a plurality of DFFs coupled thereto correspondingly;
      wherein outputs of one stage are provided to inputs of another stage to selectively reorder the ordered reception parameters based on changes in scan lines of the ultrasonic system.

14. The ultrasonic front-end of claim 13, wherein the ultrasonic front-end device is compatible with P types of reception channels where P is an integer larger than or equal to 1, wherein RC=[N, 2N, 3N, . . . , P*N] where N is an integer larger than or equal to 1, and wherein each stage of the one or more second reordering units and the one or more third reordering units comprises P*N number of 2:1 multiplexers followed with respective DFFs.

15. The ultrasonic front-end of claim 13, wherein the reception beamformer is configured to provide a binary control parameter C[K, K−1, K−2, . . . , 0] which varies as the scan lines of the ultrasonic system change, wherein each bit of the binary control parameter C[K, K−1, K−2, . . . , 0] controls P*N 2:1 multiplexers at a corresponding stage of the one or more second reordering units and the one or more third reordering units, wherein the one or more second digital reordering units and the one or more third reordering units each comprise K+1 stages, $2^{K+1} \geq P*N$, K being an integer larger than or equal to zero, and wherein inputs at an initial stage comprise the corresponding reception parameters for the RC reception channels.

16. The ultrasonic front-end of claim 15, wherein each 2:1 multiplexer of the one or more second digital reordering units and the one or more third reordering units comprises a first input and a second input, wherein signals on the second inputs of the 2:1 multiplexers are shifted $2^K$ units laterally from one stage to the next, the shift complying with a binary coding format, and wherein output from the 2:1 multiplexers at a last stage of each of the one or more second digital reordering units and the one or more third reordering units comprise P*N digitally reordered reception parameters.

17. The ultrasonic front-end of claim 8, wherein the ultrasonic transmission part comprises:
   a transmission beamformer configured to store a set of transmission parameters corresponding to respective transmission channels;
   M transmission driving units electrically connected to the transmission beamformer for driving up to M array elements in the probe of the ultrasonic system, where M is an integer larger than or equal to 1; and
   a second digital reordering unit comprising a plurality of stages, each stage of the second digital reordering unit comprising M number of 2:1 multiplexers followed with respective DFFs.

18. The ultrasonic front-end of claim 17, wherein the transmission beamformer is configured to provide a control parameter which varies as the scan lines of the ultrasonic system change, wherein each bit of the control parameter controls M 2:1 multiplexers at a corresponding stage of the second digital reordering unit, wherein inputs at an initial stage of the second reordering unit comprise the transmission parameters for M transmission channels.

19. The ultrasonic front-end of claim 18, wherein the control parameter comprises a binary control parameter B[K, K−1, K−2, . . . , 0], where $2^{K+1} \geq M$, K being an integer larger than or equal to zero and corresponding to a respective stage of the second reordering unit.

20. The ultrasonic front-end of claim 19, wherein each 2:1 multiplexer of the second reordering unit comprises a first input and a second input, wherein signals on the second inputs of the 2:1 multiplexers are shifted $2^K$ units laterally from one stage to the next in the second reordering unit, the shift complying with a binary coding format, and wherein output from the 2:1 multiplexers at a last stage of the second reordering unit comprise M digitally reordered transmission parameters.

21. A digital reordering unit of an ultrasonic system for use in an ultrasonic front-end device, comprising:
- a plurality of stages, each stage comprising a plurality of multiplexers and a plurality of D-type flip-flops (DFFs) coupled thereto correspondingly;
- wherein outputs of a first stage are provided to inputs of a second stage to selectively reorder parameters based on changes in scan lines of the ultrasonic system;
- wherein the set of ordered parameters comprises a set of reception parameters, wherein the ultrasonic front-end is connected between a probe and a detector and includes a reception beamformer configured to store the set of reception parameters corresponding to respective RC number of reception channels, wherein the reordered parameters comprise the reception parameters, wherein the ultrasonic front-end device is compatible with P types of reception channels where P is an integer larger than or equal to 1, wherein RC=[N, 2N, 3N, . . . , P*N] where N is an integer larger than or equal to 1, and wherein each stage comprises P*N number of 2:1 multiplexers followed with respective DFFs; and
- wherein the reception beamformer is configured to provide a binary control parameter C[K, K−1, K−2, . . . , 0] which varies as the scan lines of the ultrasonic system change, wherein each bit of the binary control parameter C[K, K−1, K−2, . . . , 0] controls P*N 2:1 multiplexers at a corresponding stage, wherein the digital reordering unit comprises K+1 stages, $2^{K+1} \geq P*N$, K being an integer larger than or equal to zero, and wherein inputs at the first stage comprise the reception parameters for the RC reception channels.

22. An ultrasonic front-end device, comprising:
- an ultrasonic transmission part for emitting pulses to activate currently selected transmission array elements in a probe of an ultrasonic system to transmit ultrasonic waves; and
- an ultrasonic reception part for receiving electric signals from currently selected reception array elements in the probe, the received electric signals having an order based on the currently selected reception array elements, the received electric signals corresponding to echoes of the transmitted ultrasonic waves, the ultrasonic reception part comprising a first digital reordering unit for reordering the received electrical signals, the first digital reordering unit comprising:
  - a plurality of stages, each stage comprising a plurality of multiplexers and a plurality of D-type flip-flops (DFFs) coupled thereto correspondingly;
  - wherein the received electric signals are applied to inputs of a first stage according to the order based on the currently selected reception array elements, and
  - wherein outputs of the first stage are provided to inputs of a second stage to selectively reorder the received electrical signals based on changes in scan lines of the ultrasonic system;
- M number of high-voltage isolation circuits, wherein M represents a number of array elements in the probe of the ultrasonic system;
- M number of low-voltage analog switches electrically connected to the M high-voltage isolation circuits, the M low-voltage analog switches configured to connect RC number of the array elements in the probe to RC number of respective reception channels in the ultrasonic reception part as the scan lines of the ultrasonic diagnostic system change;
- a network of resistors electrically connected to the M low-voltage analog switches;
- RC number of amplifiers electrically connected to the network of resistors, the network of resistors comprising M number of inputs IN[1, 2, 3, . . . , M] connected to respective outputs of the M low-voltage analog switches and RC number of outputs OUT[1, 2, . . . , RC] connected to respective inputs of the RC amplifiers;
- RC number of analog-to-digital converters (ADCs) electrically connected to the RC amplifiers; and
- a reception beamformer electrically connected to the RC ADCs, the reception beamformer comprising the first digital reordering unit and configured for beamforming the reordered electrical signals.

* * * * *